United States Patent
Nixon et al.

(10) Patent No.: US 10,842,653 B2
(45) Date of Patent: Nov. 24, 2020

(54) VACUUM SYSTEM FOR A PROSTHETIC FOOT

(71) Applicant: Ability Dynamics, LLC, Tempe, AZ (US)

(72) Inventors: Kodi Nixon, Mesa, AZ (US); James M. Scott, Mesa, AZ (US); Brian Werner, Mesa, AZ (US); Gene Parker, Mesa, AZ (US)

(73) Assignee: Ability Dynamics, LLC, Tempe, AZ (US)

( * ) Notice: Subject to any disclaimer, the term of this patent is extended or adjusted under 35 U.S.C. 154(b) by 94 days.

(21) Appl. No.: 16/111,569

(22) Filed: Aug. 24, 2018

(65) Prior Publication Data

US 2018/0360625 A1  Dec. 20, 2018

Related U.S. Application Data

(63) Continuation-in-part of application No. 14/976,129, filed on Dec. 21, 2015, now abandoned, which is a
(Continued)

(51) Int. Cl.
*A61F 2/66* (2006.01)
*A61F 2/68* (2006.01)
(Continued)

(52) U.S. Cl.
CPC .................. *A61F 2/66* (2013.01); *A61F 2/68* (2013.01); *A61F 2002/501* (2013.01);
(Continued)

(58) Field of Classification Search
CPC ........................... A61F 2/78–80; A43B 7/082
(Continued)

(56) References Cited

U.S. PATENT DOCUMENTS

| 3,131,307 A | 4/1964 | Bock |
| 3,331,546 A | 7/1967 | Brunelle |

(Continued)

FOREIGN PATENT DOCUMENTS

| AU | 2030483 A | 3/1984 |
| AU | 2003202173 A1 | 9/2003 |

(Continued)

*Primary Examiner* — Marcia L Watkins
(74) *Attorney, Agent, or Firm* — The Noblitt Group, PLLC

(57) ABSTRACT

A prosthetic foot comprising a vacuum system configured to attach to a vacuum attachment apparatus and a residual limb. The prosthetic foot may comprise a resilient bottom member, a resilient top member, and a vacuum system. The resilient bottom member may comprise a front end and a rear end. The resilient top member may comprise a front end and a rear end and the front end of the resilient top member may be connected to the front end of the resilient bottom member. The vacuum system may be coupled to an underside of the rear end of the top member. The vacuum system may comprise a compressible member, a chamber located within the compressible member, a valve system received within the compressible member, a passageway connecting the valve system and the chamber, and an air return coupled to the valve system and the vacuum attachment apparatus.

19 Claims, 12 Drawing Sheets

Related U.S. Application Data continuation of application No. 14/731,818, filed on Jun. 5, 2015, now abandoned, which is a continuation of application No. 13/568,535, filed on Aug. 7, 2012, now abandoned, application No. 16/111,569, which is a continuation-in-part of application No. 14/976,129, filed on Dec. 21, 2015, now abandoned, which is a continuation of application No. 14/731,818, filed on Jun. 5, 2015, now abandoned, which is a continuation of application No. 13/568,535, filed on Aug. 7, 2012, now abandoned, which is a continuation-in-part of application No. PCT/US2011/033319, filed on Apr. 20, 2011, which is a continuation-in-part of application No. 12/799,215, filed on Apr. 20, 2010, now abandoned, which is a continuation-in-part of application No. 11/901,845, filed on Sep. 19, 2007, now Pat. No. 8,048,173, application No. 16/111,569, which is a continuation-in-part of application No. 14/731,818, filed on Jun. 5, 2015, now abandoned, which is a continuation of application No. 13/568,535, filed on Aug. 7, 2012, now abandoned, which is a continuation-in-part of application No. PCT/US2011/033319, filed on Apr. 20, 2011, which is a continuation-in-part of application No. 12/799,215, filed on Apr. 20, 2010, now abandoned, which is a continuation-in-part of application No. 11/901,845, filed on Sep. 19, 2007, now Pat. No. 8,048,173, application No. 16/111,569, which is a continuation-in-part of application No. 14/731,771, filed on Jun. 5, 2015, now abandoned, which is a continuation of application No. 13/642,501, filed as application No. PCT/US2011/033319 on Apr. 20, 2011, now Pat. No. 9,078,773, which is a continuation-in-part of application No. 12/799,215, filed on Apr. 20, 2010, now abandoned, which is a continuation-in-part of application No. 11/901,845, filed on Sep. 19, 2007, now Pat. No. 8,047,173.

(60) Provisional application No. 62/550,107, filed on Aug. 25, 2017, provisional application No. 62/589,025, filed on Nov. 21, 2017.

(51) Int. Cl.
*A61F 2/80* (2006.01)
*A61F 2/74* (2006.01)
*A61F 2/50* (2006.01)

(52) U.S. Cl.
CPC .............. *A61F 2002/5009* (2013.01); *A61F 2002/6614* (2013.01); *A61F 2002/6642* (2013.01); *A61F 2002/6664* (2013.01); *A61F 2002/6671* (2013.01); *A61F 2002/742* (2013.01); *A61F 2002/748* (2013.01); *A61F 2002/802* (2013.01)

(58) Field of Classification Search
USPC ........ 623/26–46; 417/480, 478, 472; 36/3 R, 36/3 B
See application file for complete search history.

(56) References Cited

U.S. PATENT DOCUMENTS

| | | |
|---|---|---|
| 4,186,449 A | 2/1980 | Horvath |
| 4,310,932 A | 1/1982 | Nader et al. |
| 4,473,421 A | 9/1984 | Gustafsson |
| 4,497,315 A | 2/1985 | Fettweis et al. |
| 4,506,395 A | 3/1985 | Haupt |
| 4,515,153 A | 5/1985 | Calabrese |
| 4,547,913 A | 10/1985 | Phillips |
| 4,634,446 A | 1/1987 | Kristinsson |
| 4,677,969 A | 7/1987 | Calabrese |
| 4,815,471 A | 3/1989 | Stobie |
| 4,844,094 A | 7/1989 | Grim |
| 4,852,557 A | 8/1989 | Grim |
| 4,854,428 A | 8/1989 | Horvath |
| 4,856,501 A | 8/1989 | Castillo et al. |
| 4,869,267 A | 9/1989 | Grim et al. |
| 4,886,052 A | 12/1989 | Calabrese |
| 4,893,648 A | 1/1990 | Horvath |
| 4,913,755 A | 4/1990 | Grim |
| 4,923,474 A | 5/1990 | Klasson et al. |
| 4,928,678 A | 5/1990 | Grim |
| 4,940,044 A | 7/1990 | Castillo |
| 4,949,335 A | 8/1990 | Moore |
| 4,953,543 A | 9/1990 | Grim et al. |
| 4,958,705 A | 9/1990 | Horvath |
| 4,959,073 A | 9/1990 | Merlette |
| 4,977,891 A | 12/1990 | Grim |
| D314,623 S | 2/1991 | Calabrese et al. |
| 4,993,409 A | 2/1991 | Grim |
| 4,996,979 A | 3/1991 | Grim et al. |
| 5,007,937 A | 4/1991 | Fishman et al. |
| 5,027,801 A | 7/1991 | Grim |
| 5,054,475 A | 10/1991 | Calabrese et al. |
| 5,058,576 A | 10/1991 | Grim et al. |
| 5,078,128 A | 1/1992 | Grim et al. |
| 5,088,478 A | 2/1992 | Grim |
| 5,092,902 A | 3/1992 | Adams et al. |
| 5,107,824 A | 4/1992 | Rogers et al. |
| 5,108,456 A | 4/1992 | Coonan, III |
| 5,127,420 A | 7/1992 | Horvath |
| 5,135,469 A | 8/1992 | Castillo |
| 5,139,525 A | 8/1992 | Kristinsson |
| 5,156,588 A | 10/1992 | Marcune et al. |
| 5,156,631 A | 10/1992 | Merlette |
| 5,201,903 A | 4/1993 | Corbett, III et al. |
| 5,277,698 A | 1/1994 | Taylor |
| 5,288,287 A | 2/1994 | Castillo et al. |
| 5,302,169 A | 4/1994 | Taylor |
| 5,302,170 A | 4/1994 | Tweardy |
| RE34,661 E | 7/1994 | Grim |
| 5,333,604 A | 8/1994 | Green et al. |
| 5,334,135 A | 8/1994 | Grim et al. |
| 5,348,530 A | 9/1994 | Grim et al. |
| 5,353,525 A | 10/1994 | Grim |
| 5,376,131 A | 12/1994 | Lenze et al. |
| 5,376,132 A | 12/1994 | Caspers |
| 5,378,223 A | 1/1995 | Grim et al. |
| RE34,883 E | 3/1995 | Grim |
| D357,070 S | 4/1995 | Castillo |
| 5,405,409 A | 4/1995 | Knoth |
| 5,437,612 A | 8/1995 | Moore et al. |
| 5,443,521 A | 8/1995 | Knoth et al. |
| 5,445,602 A | 8/1995 | Grim et al. |
| 5,458,656 A | 10/1995 | Phillips |
| 5,462,551 A | 10/1995 | Bailey et al. |
| 5,464,385 A | 11/1995 | Grim |
| 5,468,139 A | 11/1995 | Stender |
| RE35,113 E | 12/1995 | Grim |
| 5,472,412 A | 12/1995 | Knoth |
| 5,490,832 A | 2/1996 | Brown |
| 5,515,848 A | 5/1996 | Corbett, III et al. |
| 5,529,575 A | 6/1996 | Klotz |
| 5,534,034 A | 7/1996 | Caspers |
| 5,545,233 A | 8/1996 | Fitzlaff |
| 5,549,709 A | 8/1996 | Caspers |
| 5,554,105 A | 9/1996 | Taylor |
| 5,562,605 A | 10/1996 | Taylor |
| 5,571,205 A | 11/1996 | James |
| 5,571,208 A | 11/1996 | Caspers |
| 5,593,456 A | 1/1997 | Merlette |
| 5,603,122 A | 2/1997 | Kania |
| 5,628,721 A | 5/1997 | Arnold et al. |
| 5,630,839 A | 5/1997 | Corbett, III et al. |
| 5,632,723 A | 5/1997 | Grim |
| 5,658,353 A | 8/1997 | Layton |

(56) References Cited

U.S. PATENT DOCUMENTS

| | | |
|---|---|---|
| 5,695,452 A | 12/1997 | Grim et al. |
| 5,702,489 A | 12/1997 | Slemker |
| 5,713,837 A | 2/1998 | Grim et al. |
| 5,716,335 A | 2/1998 | Iglesias et al. |
| 5,728,170 A | 3/1998 | Becker et al. |
| 5,778,565 A | 7/1998 | Holt et al. |
| 5,797,713 A | 8/1998 | Tweardy et al. |
| 5,797,864 A | 8/1998 | Taylor |
| 5,800,500 A | 9/1998 | Spelman et al. |
| 5,823,981 A | 10/1998 | Grim et al. |
| 5,851,504 A | 12/1998 | Barker et al. |
| 5,885,509 A | 3/1999 | Kristinsson |
| 5,888,212 A | 3/1999 | Petrofsky et al. |
| 5,888,217 A | 3/1999 | Slemker |
| 5,888,238 A | 3/1999 | Phillips et al. |
| 5,897,594 A | 4/1999 | Martin et al. |
| 5,904,721 A | 5/1999 | Henry et al. |
| 5,904,722 A | 5/1999 | Caspers |
| 5,931,872 A | 8/1999 | Lohmann |
| 5,951,504 A | 9/1999 | Iglesias et al. |
| 6,002,014 A | 12/1999 | Haruta et al. |
| 6,003,176 A | 12/1999 | Wasley et al. |
| 6,007,505 A | 12/1999 | Grim et al. |
| 6,013,094 A | 1/2000 | De Cubber et al. |
| 6,024,712 A | 2/2000 | Iglesias et al. |
| 6,063,125 A | 5/2000 | Arbogast et al. |
| 6,071,255 A | 6/2000 | Calabrese |
| 6,099,572 A | 8/2000 | Mosler et al. |
| 6,136,039 A | 10/2000 | Kristinsson et al. |
| 6,139,513 A | 10/2000 | Grim et al. |
| D433,756 S | 11/2000 | Castillo |
| 6,145,796 A | 11/2000 | McCraney |
| 6,149,690 A | 11/2000 | Belzidsky |
| 6,186,966 B1 | 2/2001 | Grim et al. |
| 6,231,616 B1 | 5/2001 | Helmy |
| 6,231,617 B1 | 5/2001 | Fay |
| 6,254,560 B1 | 7/2001 | Tweardy et al. |
| 6,287,345 B1 | 9/2001 | Slemker et al. |
| D452,325 S | 12/2001 | Henderson |
| 6,326,412 B1 | 12/2001 | Weber et al. |
| 6,334,876 B1 | 1/2002 | Perkins |
| 6,346,559 B1 | 2/2002 | Thiele et al. |
| 6,361,568 B1 | 3/2002 | Hoerner |
| 6,383,149 B1 | 5/2002 | DeMayo |
| 6,415,796 B1 | 7/2002 | Conrad et al. |
| 6,416,518 B1 | 7/2002 | DeMayo |
| 6,416,703 B1 | 7/2002 | Kristinsson et al. |
| 6,453,905 B1 | 9/2002 | Conrad et al. |
| 6,461,317 B1 | 10/2002 | Grim et al. |
| 6,482,167 B2 | 11/2002 | Grim et al. |
| 6,502,574 B2 | 1/2003 | Stevens et al. |
| 6,508,842 B1 | 1/2003 | Caspers |
| 6,513,530 B2 | 2/2003 | Knudson et al. |
| 6,513,531 B2 | 2/2003 | Knudson et al. |
| 6,516,806 B2 | 2/2003 | Knudson et al. |
| 6,523,541 B2 | 2/2003 | Knudson et al. |
| 6,523,542 B2 | 2/2003 | Knudson et al. |
| D473,654 S | 4/2003 | Iglesias et al. |
| 6,585,774 B2 | 7/2003 | Dean, Jr. et al. |
| 6,592,539 B1 | 7/2003 | Einarsson et al. |
| 6,596,029 B1 | 7/2003 | Gramnas |
| 6,601,584 B2 | 8/2003 | Knudson et al. |
| 6,605,118 B2 | 8/2003 | Capper et al. |
| 6,645,253 B2 | 11/2003 | Caspers |
| 6,660,204 B1 | 12/2003 | Clover, Jr. et al. |
| 6,663,581 B1 | 12/2003 | Calabrese |
| 6,666,894 B2 | 12/2003 | Perkins et al. |
| 6,685,655 B2 | 2/2004 | DeMayo |
| 6,746,414 B1 | 6/2004 | Devreese |
| 6,761,742 B2 | 7/2004 | Caspers |
| 6,767,370 B1 | 7/2004 | Mosler et al. |
| D496,106 S | 9/2004 | Iglesias et al. |
| D496,464 S | 9/2004 | Iglesias et al. |
| 6,792,699 B2 | 9/2004 | Long et al. |
| 6,797,008 B1 | 9/2004 | Arbogast et al. |
| 6,820,621 B2 | 11/2004 | DeMayo |
| 6,824,522 B2 | 11/2004 | Henderson et al. |
| D503,480 S | 3/2005 | Ingimundarson et al. |
| 6,863,695 B2 | 3/2005 | Doddroe et al. |
| D503,802 S | 4/2005 | Bjarnason |
| 6,875,187 B2 | 4/2005 | Castillo |
| 6,896,678 B2 | 5/2005 | Tweardy |
| 6,899,737 B1 | 5/2005 | Phillips et al. |
| 6,923,834 B2 | 8/2005 | Karason |
| 6,926,742 B2 | 8/2005 | Caspers et al. |
| 6,929,613 B2 | 8/2005 | Henderson et al. |
| 6,936,073 B2 | 8/2005 | Karason |
| 6,953,443 B2 | 10/2005 | Hay |
| 6,964,688 B1 | 11/2005 | Kania |
| 6,969,364 B2 | 11/2005 | Sterling |
| 6,974,484 B2 | 12/2005 | Caspers |
| 6,979,355 B1 | 12/2005 | Slemker |
| 7,001,563 B2 | 2/2006 | Janusson et al. |
| 7,004,917 B2 | 2/2006 | Henderson et al. |
| 7,018,351 B1 | 3/2006 | Iglesias et al. |
| 7,037,283 B2 | 5/2006 | Karason et al. |
| 7,037,287 B2 | 5/2006 | Cormier et al. |
| 7,044,925 B2 | 5/2006 | Castillo et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,100,225 B1 | 9/2006 | Bailey et al. |
| 7,100,613 B2 | 9/2006 | Conrad et al. |
| 7,105,122 B2 | 9/2006 | Karason |
| 7,107,180 B2 | 9/2006 | Karason |
| D533,280 S | 12/2006 | Wyatt et al. |
| 7,144,429 B2 | 12/2006 | Carstens |
| 7,150,762 B2 | 12/2006 | Caspers |
| 7,169,188 B2 | 1/2007 | Carstens |
| 7,169,189 B2 | 1/2007 | Bjarnason et al. |
| 7,169,190 B2 | 1/2007 | Phillips et al. |
| 7,172,567 B2 | 2/2007 | Lidolt et al. |
| 7,198,071 B2 | 4/2007 | Bisbee, III et al. |
| 7,198,610 B2 | 4/2007 | Ingimundarson et al. |
| 7,201,728 B2 | 4/2007 | Sterling |
| 7,217,060 B2 | 5/2007 | Ingimarsson |
| 7,223,293 B2 | 5/2007 | Kristensen |
| 7,235,108 B2 | 6/2007 | Carstens |
| 7,237,553 B2 | 7/2007 | Knudson et al. |
| 7,240,876 B2 | 7/2007 | Doubleday et al. |
| 7,255,109 B2 | 8/2007 | Knudson et al. |
| 7,255,110 B2 | 8/2007 | Knudson et al. |
| 7,288,076 B2 | 10/2007 | Grim et al. |
| 7,291,182 B1 | 11/2007 | Kania |
| RE39,961 E | 12/2007 | Petrofsky et al. |
| D557,828 S | 12/2007 | Willman |
| 7,303,538 B2 | 12/2007 | Grim et al. |
| 7,335,233 B2 | 2/2008 | Hsu et al. |
| 7,341,123 B2 | 3/2008 | Brendel et al. |
| D567,072 S | 4/2008 | Ingimundarson et al. |
| 7,371,262 B2 | 5/2008 | Lecomte et al. |
| RE40,363 E | 6/2008 | Grim et al. |
| 7,413,555 B2 | 8/2008 | Wagner et al. |
| 7,415,741 B1 | 8/2008 | Wasley et al. |
| D576,781 S | 9/2008 | Chang et al. |
| D577,828 S | 9/2008 | Ingimundarson et al. |
| 7,426,930 B1 | 9/2008 | Bailey et al. |
| 7,427,297 B2 | 9/2008 | Patterson et al. |
| 7,427,298 B1 | 9/2008 | Swanson, Sr. |
| 7,431,708 B2 | 10/2008 | Sreeramagiri |
| 7,438,843 B2 | 10/2008 | Asgeirsson |
| 7,449,005 B2 | 11/2008 | Pickering et al. |
| 7,465,281 B2 | 12/2008 | Grim et al. |
| 7,465,283 B2 | 12/2008 | Grim et al. |
| 7,468,079 B2 | 12/2008 | Collier |
| 7,479,162 B2 | 1/2009 | Kurth |
| D588,753 S | 3/2009 | Ingimundarson et al. |
| 7,513,880 B2 | 4/2009 | Ingimundarson et al. |
| D592,756 S | 5/2009 | Chang et al. |
| 7,531,006 B2 | 5/2009 | Clausen et al. |

(56) References Cited

U.S. PATENT DOCUMENTS

| | | |
|---|---|---|
| 7,544,214 B2 | 6/2009 | Gramnas |
| 7,549,970 B2 | 6/2009 | Tweardy |
| D596,301 S | 7/2009 | Campos et al. |
| 7,611,476 B2 | 11/2009 | Taranow |
| 7,631,657 B2 | 12/2009 | Alley et al. |
| 7,632,315 B2 | 12/2009 | Egilsson |
| 7,662,191 B2 | 2/2010 | Asgeirsson |
| D611,322 S | 3/2010 | Robertson |
| 7,670,385 B2 | 3/2010 | Klein |
| 7,691,154 B2 | 4/2010 | Asgeirsson et al. |
| D616,555 S | 5/2010 | Thorgilsdottir et al. |
| D616,556 S | 5/2010 | Hu |
| D616,996 S | 6/2010 | Thorgilsdottir et al. |
| D616,997 S | 6/2010 | Thorgilsdottir et al. |
| D618,359 S | 6/2010 | Einarsson |
| 7,744,653 B2 | 6/2010 | Rush et al. |
| 7,745,682 B2 | 6/2010 | Sigurjonsson et al. |
| 7,762,970 B2 | 7/2010 | Henderson et al. |
| 7,762,973 B2 | 7/2010 | Einarsson et al. |
| 7,771,487 B2 | 8/2010 | Mantelmacher |
| 7,780,741 B2 | 8/2010 | Janusson et al. |
| 7,803,301 B2 | 9/2010 | Becker et al. |
| D627,079 S | 11/2010 | Robertson |
| 7,833,181 B2 | 11/2010 | Cormier et al. |
| 7,842,099 B2 | 11/2010 | Mantelmacher |
| D628,696 S | 12/2010 | Robertson |
| D629,115 S | 12/2010 | Robertson |
| 7,867,182 B2 | 1/2011 | Iglesias et al. |
| 7,867,286 B2 | 1/2011 | Einarsson |
| 7,879,110 B2 | 2/2011 | Phillips |
| 7,883,547 B2 | 2/2011 | Mantelmacher |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,914,475 B2 | 3/2011 | Wyatt et al. |
| 7,914,586 B2 | 3/2011 | Haines |
| 7,922,775 B2 | 4/2011 | Caspers |
| 7,927,378 B2 | 4/2011 | Scussel |
| D637,942 S | 5/2011 | Lee et al. |
| 7,935,153 B2 | 5/2011 | Auberger |
| D640,380 S | 6/2011 | Tweardy et al. |
| D640,381 S | 6/2011 | Tweardy et al. |
| 7,963,998 B2 | 6/2011 | Boiten |
| D641,483 S | 7/2011 | Robertson et al. |
| 7,985,193 B2 | 7/2011 | Thorsteinsson et al. |
| D643,537 S | 8/2011 | Lee |
| D646,394 S | 10/2011 | Tweardy et al. |
| D647,623 S | 10/2011 | Thorgilsdottir et al. |
| D647,624 S | 10/2011 | Thorgilsdottir et al. |
| 8,038,636 B2 | 10/2011 | Thorgilsdottir et al. |
| 8,048,082 B1 | 11/2011 | Demayo |
| 8,052,760 B2 | 11/2011 | Egilsson et al. |
| 8,080,065 B2 | 12/2011 | Scussel et al. |
| 8,083,807 B2 | 12/2011 | Auberger et al. |
| D652,937 S | 1/2012 | Robertson et al. |
| 8,092,406 B2 | 1/2012 | Gorsen |
| 8,093,445 B2 | 1/2012 | Sigurjonsson et al. |
| 8,097,042 B2 | 1/2012 | Slemker et al. |
| 8,097,043 B2 | 1/2012 | Egilsson |
| 8,114,041 B2 | 2/2012 | Wyatt et al. |
| 8,117,720 B2 | 2/2012 | Kimes |
| 8,132,278 B1 | 3/2012 | Bailey |
| 8,177,855 B2 | 5/2012 | Asgeirsson et al. |
| D661,807 S | 6/2012 | Sigurdsson |
| 8,202,325 B2 | 6/2012 | Albrecht-Laatsch et al. |
| 8,211,187 B2 | 7/2012 | Slemker et al. |
| 8,216,166 B2 | 7/2012 | Einarsson et al. |
| D665,505 S | 8/2012 | Lee et al. |
| D665,539 S | 8/2012 | Manalo et al. |
| 8,247,635 B2 | 8/2012 | Sigurjonsson et al. |
| 8,251,928 B2 | 8/2012 | Pusch |
| 8,257,293 B2 | 9/2012 | Ingimundarson et al. |
| 8,257,446 B2 | 9/2012 | Puchhammer |
| 8,267,879 B2 | 9/2012 | Ingimundarson et al. |
| 8,273,042 B2 | 9/2012 | Lidolt et al. |
| 8,277,404 B2 | 10/2012 | Einarsson |
| 8,277,515 B2 | 10/2012 | Martin |
| 8,282,588 B2 | 10/2012 | Ingimundarson et al. |
| D671,275 S | 11/2012 | Manalo et al. |
| 8,303,670 B2 | 11/2012 | Martin et al. |
| 8,308,815 B2 | 11/2012 | Mccarthy |
| 8,308,816 B2 | 11/2012 | Slemker et al. |
| 8,317,875 B2 | 11/2012 | Jonsson et al. |
| 8,317,876 B2 | 11/2012 | Mosler |
| D672,878 S | 12/2012 | Einarsson |
| 8,328,746 B2 | 12/2012 | Ingimundarson et al. |
| 8,353,807 B2 | 1/2013 | Kruijsen et al. |
| 8,356,604 B2 | 1/2013 | Tweardy et al. |
| 8,382,852 B2 | 2/2013 | Laghi |
| 8,409,298 B2 | 4/2013 | Perkins et al. |
| 8,409,299 B2 | 4/2013 | Kurth |
| 8,410,331 B2 | 4/2013 | Janusson et al. |
| 8,425,441 B2 | 4/2013 | Ingimundarson |
| D683,465 S | 5/2013 | Forbes et al. |
| 8,444,702 B2 | 5/2013 | Slemker et al. |
| 8,454,546 B2 | 6/2013 | Campos et al. |
| 8,459,264 B2 | 6/2013 | Tweardy |
| 8,475,537 B2 | 7/2013 | King |
| 8,476,172 B2 | 7/2013 | Christof |
| 8,486,156 B2 | 7/2013 | Jonsson |
| 8,491,515 B2 | 7/2013 | Schneider |
| 8,496,715 B2 | 7/2013 | Street et al. |
| 8,505,864 B1 | 8/2013 | Taylor et al. |
| 8,517,964 B2 | 8/2013 | Sreeramagiri et al. |
| D690,473 S | 9/2013 | Manalo et al. |
| 8,523,951 B2 | 9/2013 | Kania |
| 8,530,424 B2 | 9/2013 | Lundborg |
| 8,535,390 B1 | 9/2013 | Lecomte et al. |
| 8,540,781 B2 | 9/2013 | Nissels et al. |
| 8,555,715 B2 | 10/2013 | Langlois et al. |
| 8,568,489 B2 | 10/2013 | Finlinson et al. |
| D693,930 S | 11/2013 | Manalo |
| 8,603,190 B2 | 12/2013 | Olafsson et al. |
| 8,644,921 B2 | 2/2014 | Wilson |
| 8,644,939 B2 | 2/2014 | Wilson et al. |
| 8,652,217 B2 | 2/2014 | Haynes et al. |
| 8,653,937 B2 | 2/2014 | Haynes et al. |
| 8,657,986 B2 | 2/2014 | Gansen et al. |
| 8,673,199 B2 | 3/2014 | Ottleben |
| 8,679,194 B2 | 3/2014 | Mackenzie |
| 8,701,674 B2 | 4/2014 | Tweardy et al. |
| 8,721,736 B2 | 5/2014 | Gramnas |
| 8,726,823 B2 | 5/2014 | Kristinsson |
| 8,728,171 B2 | 5/2014 | Kaltenborn et al. |
| 8,733,027 B1 | 5/2014 | Marston et al. |
| D707,830 S | 6/2014 | Klutts |
| D707,831 S | 6/2014 | Klutts |
| 8,758,449 B2 | 6/2014 | Caspers |
| 8,771,214 B2 | 7/2014 | Christenhusz et al. |
| 8,771,370 B2 | 7/2014 | Albrecht-Laatsch et al. |
| 8,771,371 B2 | 7/2014 | Tompkins |
| 8,784,501 B2 | 7/2014 | Gramnas |
| 8,789,425 B2 | 7/2014 | Oh et al. |
| D711,510 S | 8/2014 | Halldorsson |
| 8,795,386 B2 | 8/2014 | Pianykh et al. |
| 8,808,394 B2 | 8/2014 | Laghi |
| 8,821,426 B2 | 9/2014 | Einarsson et al. |
| 8,839,797 B1 | 9/2014 | Demayo |
| D714,939 S | 10/2014 | Gunnsteinsson et al. |
| 8,858,998 B2 | 10/2014 | Chu et al. |
| 8,864,692 B2 | 10/2014 | Ingimundarson et al. |
| D716,955 S | 11/2014 | Forbes et al. |
| D718,861 S | 12/2014 | Halldorsson |
| 8,906,113 B2 | 12/2014 | Mosler et al. |
| 8,915,874 B2 | 12/2014 | Schilling |
| D721,810 S | 1/2015 | Sigurdsson et al. |
| 8,940,057 B2 | 1/2015 | Asgeirsson |
| 8,951,304 B2 | 2/2015 | Wu et al. |
| 8,961,618 B2 | 2/2015 | Lecomte et al. |
| 8,992,630 B2 | 3/2015 | Olafsson et al. |
| 8,999,428 B2 | 4/2015 | Anhalt |

(56) References Cited

U.S. PATENT DOCUMENTS

| | | |
|---|---|---|
| 9,011,553 B2 | 4/2015 | Dornieden |
| 9,017,274 B2 | 4/2015 | Forbes et al. |
| 9,017,419 B1 | 4/2015 | Landry et al. |
| 9,017,420 B1 | 4/2015 | Bernhardt |
| 9,017,421 B2 | 4/2015 | Lecomte et al. |
| D729,393 S | 5/2015 | Dunn et al. |
| 9,039,644 B2 | 5/2015 | Ingimundarson et al. |
| 9,039,645 B2 | 5/2015 | Arnold et al. |
| 9,062,785 B2 | 6/2015 | Mosler et al. |
| 9,066,820 B2 | 6/2015 | Mackenzie |
| D733,883 S | 7/2015 | Omarsson et al. |
| 9,072,617 B2 | 7/2015 | Halldorsson et al. |
| 9,089,444 B2 | 7/2015 | Soss et al. |
| 9,101,323 B2 | 8/2015 | Einarsson |
| 9,168,157 B2 | 10/2015 | Mackenzie |
| 9,168,158 B2 | 10/2015 | Clausen et al. |
| D744,111 S | 11/2015 | Dunn et al. |
| 9,180,038 B2 | 11/2015 | Ingimundarson et al. |
| 9,182,210 B2 | 11/2015 | Brookover et al. |
| 9,187,613 B2 | 11/2015 | Anhalt |
| 9,192,488 B2 | 11/2015 | Bielefeld |
| D745,377 S | 12/2015 | Ressler et al. |
| D745,677 S | 12/2015 | Sigurdsson |
| 9,220,622 B2 | 12/2015 | Ingimundarson et al. |
| 9,220,624 B2 | 12/2015 | Jansson et al. |
| 9,241,812 B2 | 1/2016 | Martin et al. |
| 9,241,813 B2 | 1/2016 | Hillmann |
| 9,248,032 B2 | 2/2016 | Gunnarsson et al. |
| 9,259,332 B2 | 2/2016 | Danzig et al. |
| 9,259,333 B2 | 2/2016 | Mackenzie et al. |
| 9,265,626 B1 | 2/2016 | Lecomte et al. |
| 9,265,628 B2 | 2/2016 | Tompkins et al. |
| 9,265,629 B2 | 2/2016 | Kelley et al. |
| 9,265,644 B2 | 2/2016 | Einarsson et al. |
| 9,265,645 B2 | 2/2016 | Ingimundarson et al. |
| 9,271,850 B2 | 3/2016 | Seyr et al. |
| 9,272,409 B2 | 3/2016 | Suhami |
| 9,278,013 B2 | 3/2016 | Seyr et al. |
| D753,837 S | 4/2016 | Sigurdsson et al. |
| 9,345,590 B2 | 5/2016 | Arabian et al. |
| 9,345,591 B2 | 5/2016 | Bisbee, III et al. |
| 9,345,605 B2 | 5/2016 | Dunn et al. |
| 9,351,854 B2 | 5/2016 | Jonsson et al. |
| 9,351,864 B2 | 5/2016 | Romo et al. |
| 9,358,138 B2 | 6/2016 | Kelley et al. |
| 9,370,440 B2 | 6/2016 | Ingimundarson et al. |
| 9,387,096 B2 | 7/2016 | Sverrisson et al. |
| 9,393,132 B2 | 7/2016 | Kranner et al. |
| 9,408,726 B2 | 8/2016 | Rowe, Jr. et al. |
| 9,427,338 B2 | 8/2016 | Clausen et al. |
| 9,439,786 B2 | 9/2016 | Nijman et al. |
| 9,468,554 B2 | 10/2016 | Petursson et al. |
| 9,474,636 B2 | 10/2016 | Sandahl et al. |
| 9,498,355 B2 | 11/2016 | Halldorsson |
| 9,510,948 B2 | 12/2016 | Padala |
| 9,510,967 B2 | 12/2016 | Lee et al. |
| D776,289 S | 1/2017 | Dunn et al. |
| 9,532,895 B2 | 1/2017 | Romo |
| 9,539,135 B2 | 1/2017 | Romo et al. |
| 9,554,923 B2 | 1/2017 | Kettwig et al. |
| 9,554,935 B2 | 1/2017 | Ingimundarson et al. |
| 9,579,220 B2 | 2/2017 | Jonsson et al. |
| 9,579,221 B2 | 2/2017 | Mosler et al. |
| 9,589,698 B2 | 3/2017 | Anhalt et al. |
| 9,597,786 B2 | 3/2017 | Romo et al. |
| 9,603,725 B2 | 3/2017 | Forster et al. |
| 9,610,177 B2 | 4/2017 | Duger |
| 9,615,945 B2 | 4/2017 | Mosler et al. |
| 9,622,899 B2 | 4/2017 | Romo et al. |
| 9,636,240 B2 | 5/2017 | Reinelt |
| 9,668,903 B2 | 6/2017 | Hsu et al. |
| 9,675,472 B2 | 6/2017 | Mackenzie |
| 9,681,964 B2 | 6/2017 | Mackenzie |
| 9,687,365 B2 | 6/2017 | Asgeirsson et al. |
| 9,707,107 B2 | 7/2017 | Ingimarsson |
| D795,433 S | 8/2017 | Clausen et al. |
| 9,717,606 B2 | 8/2017 | Gramnaes |
| 9,730,814 B2 | 8/2017 | Omarsson et al. |
| 9,737,420 B2 | 8/2017 | Van Der Watt et al. |
| D797,292 S | 9/2017 | Clausen et al. |
| 9,751,243 B2 | 9/2017 | Kroll-Orywahl et al. |
| 9,763,808 B2 | 9/2017 | Jonsson |
| 9,763,810 B2 | 9/2017 | Hines |
| 9,770,891 B2 | 9/2017 | Bjarnason et al. |
| 9,775,715 B2 | 10/2017 | Boiten |
| 9,782,276 B2 | 10/2017 | Gottlieb et al. |
| 9,788,977 B2 | 10/2017 | Halldorsson et al. |
| 9,788,986 B2 | 10/2017 | Dunn |
| 9,788,988 B2 | 10/2017 | Kompa |
| 9,808,358 B2 | 11/2017 | Mosler et al. |
| 9,814,606 B2 | 11/2017 | Danzig et al. |
| 9,820,873 B2 | 11/2017 | Sandahl |
| 9,839,536 B2 | 12/2017 | Bergande |
| 9,839,548 B2 | 12/2017 | Ingvarsson et al. |
| 9,839,549 B2 | 12/2017 | Walborn et al. |
| 9,844,448 B2 | 12/2017 | Karlsson et al. |
| 9,844,450 B2 | 12/2017 | Kranner et al. |
| 9,872,792 B2 | 1/2018 | Romo et al. |
| 9,877,851 B2 | 1/2018 | Egilsson et al. |
| D810,309 S | 2/2018 | Forbes et al. |
| 9,889,034 B2 | 2/2018 | Gunnsteinsson |
| 9,907,687 B2 | 3/2018 | Ingimundarson et al. |
| 9,925,071 B2 | 3/2018 | Langlois et al. |
| 9,943,420 B2 | 4/2018 | Leiniger et al. |
| 9,943,431 B2 | 4/2018 | Chang et al. |
| 9,968,469 B2 | 5/2018 | Muller et al. |
| 9,987,158 B2 | 6/2018 | Ingimundarson et al. |
| 9,993,357 B2 | 6/2018 | Jonsson |
| 9,993,381 B2 | 6/2018 | Blackwell et al. |
| 9,999,523 B2 | 6/2018 | Lecomte et al. |
| 10,010,434 B2 | 7/2018 | Thorsteinsson et al. |
| 10,010,435 B2 | 7/2018 | Schuh et al. |
| 10,034,782 B2 | 7/2018 | Sandahl |
| 10,039,653 B2 | 8/2018 | Kelley et al. |
| 10,051,923 B2 | 8/2018 | Omarsson et al. |
| 10,052,221 B2 | 8/2018 | Albertsson et al. |
| 10,064,749 B2 | 9/2018 | Hu et al. |
| 10,092,424 B2 | 10/2018 | Bache |
| 10,117,758 B2 | 11/2018 | Clausen et al. |
| 10,123,889 B2 | 11/2018 | Egilsson et al. |
| 10,143,268 B2 | 12/2018 | Romo et al. |
| 10,143,581 B2 | 12/2018 | Chetlapalli et al. |
| 2002/0040249 A1 | 4/2002 | Phillips |
| 2002/0198245 A1 | 12/2002 | Haruta et al. |
| 2004/0024322 A1 | 2/2004 | Caspers |
| 2004/0068325 A1 | 4/2004 | Phillips et al. |
| 2004/0137178 A1 | 7/2004 | Janusson et al. |
| 2004/0163278 A1 | 8/2004 | Caspers et al. |
| 2004/0181290 A1 | 9/2004 | Caspers |
| 2004/0226115 A1 | 11/2004 | Gunnsteinsson et al. |
| 2005/0038525 A1 | 2/2005 | Doddroe et al. |
| 2005/0071018 A1 | 3/2005 | Phillips et al. |
| 2005/0101693 A1 | 5/2005 | Arbogast et al. |
| 2005/0101896 A1 | 5/2005 | Calabrese |
| 2005/0229317 A1 | 10/2005 | Heiser et al. |
| 2005/0234275 A1 | 10/2005 | Luo et al. |
| 2005/0234374 A1 | 10/2005 | Grim et al. |
| 2005/0234375 A1 | 10/2005 | Grim et al. |
| 2005/0267547 A1 | 12/2005 | Knudson et al. |
| 2005/0283257 A1 | 12/2005 | Bisbee, III et al. |
| 2006/0212128 A1 | 9/2006 | Nachbar |
| 2007/0055383 A1 | 3/2007 | King |
| 2007/0055384 A1 | 3/2007 | Perkins et al. |
| 2007/0080479 A1 | 4/2007 | Arbogast et al. |
| 2007/0144538 A1 | 6/2007 | Tweardy |
| 2007/0196222 A1* | 8/2007 | Mosler .................. F04B 33/00 417/472 |
| 2007/0213829 A1 | 9/2007 | Le Couedic et al. |
| 2007/0213839 A1 | 9/2007 | Nachbar |
| 2008/0188949 A1 | 8/2008 | MacKenzie |
| 2009/0036998 A1* | 2/2009 | Finlinson ................ F04B 45/04 623/34 |
| 2009/0076625 A1 | 3/2009 | Groves et al. |
| 2009/0182435 A1 | 7/2009 | Haberman |

(56) References Cited

U.S. PATENT DOCUMENTS

| | | |
|---|---|---|
| 2009/0240344 A1 | 9/2009 | Colvin et al. |
| 2009/0292370 A1 | 11/2009 | Pusch et al. |
| 2010/0030342 A1 | 2/2010 | Oddsson et al. |
| 2010/0042227 A1 | 2/2010 | Schmidt |
| 2010/0070051 A1 | 3/2010 | Carstens |
| 2010/0139530 A1 | 6/2010 | Ceballos-Godefroy |
| 2011/0034844 A1 | 2/2011 | Thorgilsdottir et al. |
| 2011/0146032 A1 | 6/2011 | Hu et al. |
| 2011/0229113 A1 | 9/2011 | Kurth et al. |
| 2011/0270413 A1 | 11/2011 | Haynes |
| 2012/0000092 A1 | 1/2012 | Ingvarsson et al. |
| 2012/0055616 A1 | 3/2012 | Clausen |
| 2012/0123559 A1 | 5/2012 | Mosler et al. |
| 2012/0165958 A1 | 6/2012 | Clausen et al. |
| 2012/0226364 A1 | 9/2012 | Kampas et al. |
| 2012/0226365 A1 | 9/2012 | Seyr et al. |
| 2012/0232674 A1 | 9/2012 | Kampas et al. |
| 2012/0253475 A1 | 10/2012 | Kelley et al. |
| 2013/0006156 A1 | 1/2013 | Ingimundarson et al. |
| 2013/0079892 A1 | 3/2013 | Imhof |
| 2013/0103125 A1 | 4/2013 | Radspieler et al. |
| 2013/0110257 A1 | 5/2013 | Slemker et al. |
| 2013/0144197 A1 | 6/2013 | Ingimundarson et al. |
| 2013/0144402 A1 | 6/2013 | Clausen et al. |
| 2013/0173020 A1 | 7/2013 | Slemker et al. |
| 2013/0190895 A1 | 7/2013 | Kristinsdottir |
| 2013/0331951 A1 | 12/2013 | Doddroe et al. |
| 2014/0012397 A1 | 1/2014 | Mosler et al. |
| 2014/0018938 A1 | 1/2014 | Bertels et al. |
| 2014/0046456 A1 | 2/2014 | Smith |
| 2014/0063220 A1 | 3/2014 | Taylor |
| 2014/0067085 A1 | 3/2014 | Doddroe et al. |
| 2014/0116452 A1 | 5/2014 | Ingimundarson et al. |
| 2014/0174849 A1 | 6/2014 | Gansen |
| 2014/0188251 A1 | 7/2014 | Mosler et al. |
| 2014/0228726 A1 | 8/2014 | Kruijsen et al. |
| 2014/0276300 A1 | 9/2014 | Reinhardt et al. |
| 2014/0288668 A1 | 9/2014 | Gottlieb et al. |
| 2015/0032041 A1 | 1/2015 | Ingimundarson et al. |
| 2015/0032225 A1 | 1/2015 | Oddsson et al. |
| 2015/0073566 A1 | 3/2015 | Ragnarsdottir et al. |
| 2015/0075030 A1 | 3/2015 | Walborn et al. |
| 2015/0075537 A1 | 3/2015 | Demayo |
| 2015/0079014 A1 | 3/2015 | Ingvarsson et al. |
| 2015/0099253 A1 | 4/2015 | De Roy |
| 2015/0121657 A1 | 5/2015 | Ingimundarson et al. |
| 2015/0164660 A1 | 6/2015 | Will et al. |
| 2015/0164661 A1 | 6/2015 | Ragnarsdottir et al. |
| 2015/0197324 A1 | 7/2015 | Marlin |
| 2015/0202452 A1 | 7/2015 | Skiera et al. |
| 2015/0230943 A1 | 8/2015 | Marlin et al. |
| 2015/0230944 A1 | 8/2015 | Mosler et al. |
| 2015/0230945 A1 | 8/2015 | Bache et al. |
| 2015/0250624 A1 | 9/2015 | Mosler et al. |
| 2015/0262319 A1 | 9/2015 | Tuttle |
| 2015/0265426 A1 | 9/2015 | Clausen |
| 2015/0265429 A1 | 9/2015 | Jonsson et al. |
| 2015/0289999 A1 | 10/2015 | Radspieler |
| 2015/0297368 A1 | 10/2015 | Langlois |
| 2015/0297369 A1 | 10/2015 | Mosler et al. |
| 2015/0328020 A1 | 11/2015 | Clausen et al. |
| 2015/0366680 A1 | 12/2015 | Accinni et al. |
| 2015/0366736 A1 | 12/2015 | Chetlapalli et al. |
| 2016/0000584 A1 | 1/2016 | Brown |
| 2016/0008147 A1 | 1/2016 | Marlin |
| 2016/0008148 A1 | 1/2016 | Tompkins |
| 2016/0008157 A1 | 1/2016 | Brookover et al. |
| 2016/0009523 A1 | 1/2016 | Omarsson et al. |
| 2016/0009526 A1 | 1/2016 | Mertala et al. |
| 2016/0022442 A1 | 1/2016 | Kettwig et al. |
| 2016/0030203 A1 | 2/2016 | Pusch et al. |
| 2016/0067077 A1 | 3/2016 | Lidolt et al. |
| 2016/0095734 A1 | 4/2016 | Sigurdsson et al. |
| 2016/0120665 A1 | 5/2016 | Muller |
| 2016/0120683 A1 | 5/2016 | Romo et al. |
| 2016/0143764 A1 | 5/2016 | Klutts |
| 2016/0151189 A1 | 6/2016 | Romo et al. |
| 2016/0184112 A1 | 6/2016 | Radspieler |
| 2016/0184113 A1 | 6/2016 | Koniuk |
| 2016/0213823 A1 | 7/2016 | Walborn et al. |
| 2016/0220375 A1 | 8/2016 | Omarsson et al. |
| 2016/0220409 A1 | 8/2016 | Romo et al. |
| 2016/0228114 A1 | 8/2016 | Demayo |
| 2016/0242939 A1 | 8/2016 | Haynes |
| 2016/0250045 A1 | 9/2016 | Colvin et al. |
| 2016/0250061 A1 | 9/2016 | Ingimundarson et al. |
| 2016/0262499 A1 | 9/2016 | Lee et al. |
| 2016/0278959 A1 | 9/2016 | Omarsson et al. |
| 2016/0278963 A1 | 9/2016 | Webster et al. |
| 2016/0287237 A1 | 10/2016 | Demayo et al. |
| 2016/0287238 A1 | 10/2016 | Demayo et al. |
| 2016/0287424 A1 | 10/2016 | Webster et al. |
| 2016/0296359 A1 | 10/2016 | Stefansson et al. |
| 2016/0296360 A1 | 10/2016 | Ingimundarson et al. |
| 2016/0296401 A1 | 10/2016 | Cole et al. |
| 2016/0324678 A1 | 11/2016 | Ingimundarson et al. |
| 2016/0346100 A1 | 12/2016 | Sverrisson et al. |
| 2016/0346112 A1 | 12/2016 | Ingimundarson et al. |
| 2016/0346150 A1 | 12/2016 | Blackwell et al. |
| 2017/0007435 A1 | 1/2017 | Klutts |
| 2017/0020694 A1 | 1/2017 | Tompkins |
| 2017/0027716 A1 | 2/2017 | Friesen et al. |
| 2017/0027719 A1 | 2/2017 | Bache et al. |
| 2017/0027731 A1 | 2/2017 | Jonsson et al. |
| 2017/0030694 A1 | 2/2017 | Mykkanen |
| 2017/0035583 A1 | 2/2017 | Monicke et al. |
| 2017/0035585 A1 | 2/2017 | Lundborg |
| 2017/0035586 A1 | 2/2017 | Egilsson et al. |
| 2017/0042703 A1 | 2/2017 | Pusch et al. |
| 2017/0042742 A1 | 2/2017 | Demayo |
| 2017/0049584 A1 | 2/2017 | Pusch et al. |
| 2017/0049654 A1 | 2/2017 | Demayo et al. |
| 2017/0056210 A1 | 3/2017 | Jonasson et al. |
| 2017/0079811 A1 | 3/2017 | Kelley et al. |
| 2017/0095354 A1 | 4/2017 | Pusch et al. |
| 2017/0105853 A1 | 4/2017 | Jonsson et al. |
| 2017/0112640 A1 | 4/2017 | Clausen et al. |
| 2017/0119552 A1 | 5/2017 | Clausen et al. |
| 2017/0119569 A1 | 5/2017 | Hsu et al. |
| 2017/0135448 A1 | 5/2017 | Ingimundarson et al. |
| 2017/0143519 A1 | 5/2017 | Muller et al. |
| 2017/0151073 A1 | 6/2017 | Halldorsson |
| 2017/0156893 A1 | 6/2017 | Olafsson et al. |
| 2017/0156911 A1 | 6/2017 | Ingimundarson et al. |
| 2017/0156963 A1 | 6/2017 | Tuttemann et al. |
| 2017/0165095 A1 | 6/2017 | Romo et al. |
| 2017/0189220 A1 | 7/2017 | Ingimundarson et al. |
| 2017/0202687 A1 | 7/2017 | Anhalt et al. |
| 2017/0231788 A1 | 8/2017 | Kelley et al. |
| 2017/0231796 A1 | 8/2017 | Romo et al. |
| 2017/0239118 A1 | 8/2017 | Cole et al. |
| 2017/0246022 A1 | 8/2017 | Calco et al. |
| 2017/0252198 A1 | 9/2017 | Thorsteinsdottir et al. |
| 2017/0252249 A1 | 9/2017 | Cole et al. |
| 2017/0254004 A1 | 9/2017 | Rockstroh et al. |
| 2017/0266028 A1 | 9/2017 | Thorgilsdottir et al. |
| 2017/0281373 A1 | 10/2017 | Schober et al. |
| 2017/0281389 A1 | 10/2017 | Frost et al. |
| 2017/0298981 A1 | 10/2017 | Asgeirsson |
| 2017/0304081 A1 | 10/2017 | Pusch et al. |
| 2017/0304083 A1 | 10/2017 | Clausen |
| 2017/0304085 A1 | 10/2017 | Kurth |
| 2017/0312158 A1 | 11/2017 | Blackwell |
| 2017/0319286 A1 | 11/2017 | Jansen et al. |
| 2017/0325974 A1 | 11/2017 | Lincoln et al. |
| 2017/0325984 A1 | 11/2017 | Walborn et al. |
| 2017/0333221 A1 | 11/2017 | Lecomte et al. |
| 2017/0340469 A1 | 11/2017 | Huffa et al. |
| 2017/0347904 A1 | 12/2017 | Wilson |
| 2017/0348131 A1 | 12/2017 | Petursson et al. |
| 2017/0360580 A1 | 12/2017 | Karlsson et al. |
| 2017/0367851 A1 | 12/2017 | Lincoln et al. |
| 2017/0367853 A1 | 12/2017 | Dressler et al. |
| 2017/0367854 A1 | 12/2017 | King |

(56) References Cited

U.S. PATENT DOCUMENTS

| | | | |
|---|---|---|---|
| 2018/0000614 A1 | 1/2018 | Shen | |
| 2018/0000623 A1 | 1/2018 | Ingimundarson et al. | |
| 2018/0008436 A1 | 1/2018 | Sandahl | |
| 2018/0036149 A1 | 2/2018 | Harris | |
| 2018/0036151 A1 | 2/2018 | Garus et al. | |
| 2018/0036152 A1 | 2/2018 | Klutts | |
| 2018/0042654 A1 | 2/2018 | Ingvarsson et al. | |
| 2018/0042749 A1 | 2/2018 | Ingimundarson | |
| 2018/0042752 A1 | 2/2018 | Omarsson et al. | |
| 2018/0042754 A1 | 2/2018 | Ingimundarson et al. | |
| 2018/0049904 A1 | 2/2018 | Ingimundarson et al. | |
| 2018/0055659 A1 | 3/2018 | Sandahl et al. | |
| 2018/0055661 A1 | 3/2018 | Erdmann et al. | |
| 2018/0110642 A1 | 4/2018 | Sorrenti et al. | |
| 2018/0147080 A1 | 5/2018 | Thorsteinsdottir et al. | |
| 2018/0153715 A1 | 6/2018 | Jonsson et al. | |
| 2018/0177617 A1 | 6/2018 | Pusch et al. | |
| 2018/0177618 A1 | 6/2018 | Langlois et al. | |
| 2018/0185176 A1 | 7/2018 | Jonsson et al. | |
| 2018/0185186 A1 | 7/2018 | Chetlapalli et al. | |
| 2018/0193173 A1 | 7/2018 | Sverrisson et al. | |
| 2018/0200083 A1 | 7/2018 | Egilsson et al. | |
| 2018/0214284 A1 | 8/2018 | Wagner et al. | |
| 2018/0221176 A1 | 8/2018 | Halldorsson et al. | |
| 2018/0235784 A1 | 8/2018 | Halldorsson et al. | |
| 2018/0235785 A1 | 8/2018 | Bache et al. | |
| 2018/0256373 A1 | 9/2018 | Birgisdottir et al. | |
| 2018/0256380 A1 | 9/2018 | Pusch et al. | |
| 2018/0263793 A1 | 9/2018 | Clausen et al. | |
| 2018/0271678 A1 | 9/2018 | Clausen | |
| 2018/0271679 A1 | 9/2018 | Caldwell et al. | |
| 2018/0280183 A1 | 10/2018 | Ingimundarson et al. | |
| 2018/0281340 A1 | 10/2018 | Brienza et al. | |
| 2018/0289514 A1 | 10/2018 | Chabloz et al. | |
| 2018/0296370 A1 | 10/2018 | Jonsson et al. | |
| 2018/0296371 A1 | 10/2018 | Jonasson et al. | |
| 2018/0325212 A1 | 11/2018 | Walborn et al. | |

FOREIGN PATENT DOCUMENTS

| | | | |
|---|---|---|---|
| AU | 2003202173 B | 9/2007 | |
| BR | 102012030461 A | 9/2014 | |
| BR | 102012030461 A2 | 9/2014 | |
| CA | 1309627 C | 11/1992 | |
| CA | 2042431 A | 11/1992 | |
| CA | 2042431 A1 | 11/1992 | |
| CA | 10309627 C | 11/1992 | |
| CA | 2108495 A | 4/1995 | |
| CA | 2108495 A1 | 4/1995 | |
| CA | 2174151 C | 1/2000 | |
| CA | 2290414 C | 8/2004 | |
| CA | 2237880 C | 5/2006 | |
| CA | 2864208 A | 8/2014 | |
| CA | 2864208 A1 | 8/2014 | |
| CN | 1146204 A | 3/1997 | |
| CN | 101257868 A | 9/2008 | |
| CN | 100536806 C | 9/2009 | |
| CN | 204562471 U | 8/2015 | |
| CN | 204839841 U | 12/2015 | |
| CN | 205758773 U | 12/2016 | |
| CN | 205866901 U | 1/2017 | |
| CN | 106798602 A | 6/2017 | |
| CN | 206299731 U | 7/2017 | |
| CN | 104394807 B | 8/2017 | |
| CN | 104394807 B8 | 8/2017 | |
| CN | 106667629 B | 4/2018 | |
| DE | 470581 C | 1/1929 | |
| DE | 1855981 U | 8/1962 | |
| DE | 1872483 U | 5/1963 | |
| DE | 2801299 C | 6/1982 | |
| DE | 2801299 C2 | 6/1982 | |
| DE | 7800863 U | 1/1983 | |
| DE | 7800863 U1 | 1/1983 | |
| DE | 59400260 | 6/1996 | |
| DE | 59308220 | 4/1998 | |
| DE | 59308220 | 9/1998 | |
| DE | 29823435 U1 | 7/1999 | |
| DE | 29823435 U | 9/1999 | |
| DE | 19817445 A | 10/1999 | |
| DE | 19817445 A1 | 10/1999 | |
| DE | 59805657 | 10/2002 | |
| DE | 59911786 | 4/2005 | |
| DE | 10153796 B | 10/2005 | |
| DE | 10153796 B4 | 10/2005 | |
| DE | 10000495 B | 3/2006 | |
| DE | 10000495 B4 | 3/2006 | |
| DE | 10118101 B | 5/2006 | |
| DE | 10118101 B4 | 5/2006 | |
| DE | 202008014651 U | 1/2009 | |
| DE | 202008014651 U1 | 1/2009 | |
| DE | 202008014677 U | 1/2009 | |
| DE | 202008014677 U1 | 1/2009 | |
| DE | 102008058039 A | 5/2010 | |
| DE | 102008058039 A1 | 5/2010 | |
| DE | 202011001473 U1 | 5/2011 | |
| DE | 202011001473 U | 6/2011 | |
| DE | 102010020262 B | 12/2011 | |
| DE | 102010020262 B4 | 12/2011 | |
| DE | 202012001258 U | 3/2012 | |
| DE | 202012001258 U1 | 3/2012 | |
| DE | 102010045469 B | 5/2012 | |
| DE | 102010045469 B4 | 5/2012 | |
| DE | 102011105488 A | 12/2012 | |
| DE | 102011105488 A1 | 12/2012 | |
| DE | 102011119593 B | 12/2013 | |
| DE | 102011119593 B4 | 12/2013 | |
| DE | 59807695 C | 1/2015 | |
| DE | 59807695 C5 | 1/2015 | |
| DE | 10212011681 B | 4/2015 | |
| DE | 102012011681 B4 | 4/2015 | |
| DE | 102014113157 B | 2/2016 | |
| DE | 102014113157 B3 | 2/2016 | |
| DE | 102014116240 B | 6/2016 | |
| DE | 102014116240 B4 | 6/2016 | |
| DE | 102016107743 A | 10/2017 | |
| DE | 102016107743 A1 | 10/2017 | |
| DE | 102016111018 B | 12/2017 | |
| DE | 102016111018 B3 | 12/2017 | |
| DE | 102016118032 A | 1/2018 | |
| DE | 102016118032 A1 | 1/2018 | |
| EP | 0119231 A | 9/1984 | |
| EP | 0119231 A1 | 9/1984 | |
| EP | 0315675 A | 11/1990 | |
| EP | 0315675 A4 | 11/1990 | |
| EP | 0312515 B | 5/1992 | |
| EP | 0312515 B1 | 5/1992 | |
| EP | 0681818 B | 7/2000 | |
| EP | 0681818 B1 | 7/2000 | |
| EP | 1006960 B | 1/2003 | |
| EP | 1006960 B1 | 1/2003 | |
| EP | 0965435 B | 3/2005 | |
| EP | 0965435 B1 | 3/2005 | |
| EP | 1216013 B | 6/2006 | |
| EP | 1216013 B1 | 6/2006 | |
| EP | 1263356 B | 1/2010 | |
| EP | 1263356 B1 | 1/2010 | |
| EP | 1322267 B | 3/2011 | |
| EP | 1322267 B1 | 3/2011 | |
| EP | 1539057 B | 9/2012 | |
| EP | 1539057 B1 | 9/2012 | |
| EP | 0762857 B | 10/2012 | |
| EP | 0762857 B2 | 10/2012 | |
| EP | 2040649 B | 10/2012 | |
| EP | 2040649 B1 | 10/2012 | |
| EP | 1904773 B | 11/2012 | |
| EP | 1904773 B1 | 11/2012 | |
| EP | 2358268 A | 7/2014 | |
| EP | 2358268 A4 | 7/2014 | |
| EP | 2512387 B | 9/2015 | |
| EP | 2512387 B1 | 9/2015 | |
| EP | 2536366 B | 9/2015 | |
| EP | 2536366 B1 | 9/2015 | |
| EP | 2815728 B | 1/2016 | |
| EP | 2815728 B1 | 1/2016 | |

(56) References Cited

FOREIGN PATENT DOCUMENTS

| | | | |
|---|---|---|---|
| EP | 2890295 A | 6/2016 |
| EP | 2890295 A4 | 6/2016 |
| EP | 1933775 B | 8/2016 |
| EP | 1933775 B1 | 8/2016 |
| EP | 2816978 B | 1/2017 |
| EP | 2816978 B1 | 1/2017 |
| EP | 3193794 A | 7/2017 |
| EP | 3193794 A1 | 7/2017 |
| EP | 3034044 B | 10/2017 |
| EP | 3034044 B1 | 10/2017 |
| EP | 3205221 B | 3/2018 |
| EP | 3205221 B1 | 3/2018 |
| EP | 3298991 A | 3/2018 |
| EP | 3298991 A1 | 3/2018 |
| EP | 3188697 A | 4/2018 |
| EP | 3188697 A4 | 4/2018 |
| EP | 3328327 A | 6/2018 |
| EP | 3328327 A1 | 6/2018 |
| ES | 235931 T | 3/2011 |
| ES | 2353931 T3 | 3/2011 |
| FR | 2345138 B | 4/1982 |
| FR | 2345138 B1 | 4/1982 |
| GB | 2012589 A | 8/1979 |
| GB | 9922952 | 12/1999 |
| GB | 2353475 A | 2/2001 |
| IL | 117003 A | 10/2000 |
| IN | 198360 A | 7/2009 |
| IN | 198360 A1 | 7/2009 |
| JP | H0822295 B2 | 3/1996 |
| JP | 0822295 B | 5/1996 |
| JP | 08131466 A | 5/1996 |
| JP | H08131466 A | 5/1996 |
| JP | 2958257 B | 8/2007 |
| JP | 3958257 B2 | 8/2007 |
| JP | 4646318 B | 3/2011 |
| JP | 4646319 B2 | 3/2011 |
| KR | 100445086 B | 8/2005 |
| KR | 100445086 B1 | 8/2005 |
| KR | 101330740 B | 11/2013 |
| KR | 101330740 B1 | 11/2013 |
| KR | 101515254 B | 4/2015 |
| KR | 101515254 B1 | 4/2015 |
| NL | 1031419 C | 9/2007 |
| NL | 1031419 C2 | 9/2007 |
| NO | 315635 B | 7/2003 |
| NO | 315635 B1 | 10/2003 |
| SE | 434928 B | 8/1984 |
| SE | 434928 B | 9/1984 |
| SE | 8405072 | 10/1984 |
| SE | 469817 B | 9/1993 |
| TW | 267100 B | 1/1996 |
| TW | 343917 B | 11/1998 |
| TW | 398902 U | 3/2011 |
| TW | M398902 U | 3/2011 |
| WO | 9406375 A1 | 3/1994 |
| WO | 9418863 A1 | 9/1994 |
| WO | 9418863 A9 | 10/1994 |
| WO | 9622864 A1 | 8/1996 |
| WO | 9808470 A1 | 3/1998 |
| WO | 9808470 A9 | 5/1998 |
| WO | 0074611 A2 | 12/2000 |
| WO | 0129120 A1 | 4/2001 |
| WO | 0129128 A1 | 4/2001 |
| WO | 0226158 A2 | 4/2002 |
| WO | 2002026158 A2 | 4/2002 |
| WO | 03034904 A9 | 5/2004 |
| WO | 2004112663 A1 | 12/2004 |
| WO | 2005102208 A2 | 11/2005 |
| WO | 2009121615 A2 | 10/2009 |
| WO | 2011029425 A2 | 3/2011 |
| WO | 2012031707 A1 | 3/2012 |
| WO | 2013124057 A1 | 8/2013 |
| WO | 2014000066 A1 | 1/2014 |
| WO | 2015169289 A1 | 11/2015 |
| WO | 2016020244 A1 | 2/2016 |
| WO | 2017147167 A1 | 8/2017 |
| WO | 2017157875 A1 | 9/2017 |
| WO | 2017162855 A1 | 9/2017 |
| WO | 2017186680 A1 | 11/2017 |
| WO | 2017186902 A1 | 11/2017 |
| WO | 2017194479 A1 | 11/2017 |
| WO | 2017216151 A2 | 12/2017 |
| WO | 2018019637 A1 | 2/2018 |

\* cited by examiner

VACUUM SYSTEM FOR A PROSTHETIC FOOT

CROSS-REFERENCES TO RELATED APPLICATIONS

The present application claims the benefit of U.S. Provisional Application Ser. No. 62/550,107, filed Aug. 25, 2017 and U.S. Provisional Application Ser. No. 62/589,025, filed Nov. 21, 2017; and is a continuation in part of U.S. patent application Ser. No. 14/976,129, filed Dec. 21, 2015, which is a continuation of U.S. patent application Ser. No. 14/731,818, filed Jun. 5, 2015, which is a continuation of U.S. patent application Ser. No. 13/568,535, filed on Aug. 7, 2012; and this application is a continuation in part of U.S. patent application Ser. No. 14/976,129, filed Dec. 21, 2015, which is a continuation of U.S. patent application Ser. No. 14/731,818, filed Jun. 5, 2015, which is a continuation of U.S. patent application Ser. No. 13/568,535, filed on Aug. 7, 2012, which is a continuation-in-part of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173; and this application is a continuation in part of U.S. patent application Ser. No. 14/731,818, filed Jun. 5, 2015, which is a continuation of U.S. patent application Ser. No. 13/568,535, filed on Aug. 7, 2012, which is a continuation-in-part of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173; and this application is a continuation-in-part of U.S. patent application Ser. No. 14/731,771, filed Jun. 5, 2015, which is a continuation of U.S. patent application Ser. No. 13/642,501, filed on Nov. 27, 2012, now U.S. Pat. No. 9,078,773, which is a 371 national phase application of International Application No. PCT/US11/33319, filed on Apr. 20, 2011, which is a continuation-in-part of U.S. patent application Ser. No. 12/799,215, filed on Apr. 20, 2010, which is a continuation-in-part of U.S. patent application Ser. No. 11/901,845, filed on Sep. 19, 2007, now U.S. Pat. No. 8,048,173 and incorporates the disclosure of all such applications by reference, and this application incorporates the disclosure of all such applications by reference.

BACKGROUND

Prosthetic feet are well known in the art. In use, such prosthetic feet are typically mounted to either an above knee amputation socket or a below knee amputation socket and are designed to mimic the natural gait of a user. Traditionally, the sockets of most amputation types are retained on the user through friction. This friction has been achieved by using socks or liners of various specialized materials. The major drawback with this system has been that over the course of a day, the amputated limb will change its volume, and the friction force will change accordingly. Replacing the friction retention system with a vacuum retention system has proven to be advantageous to the user for many reasons. The biggest reason being that vacuum helps the limb volume to remain more stable which improves socket retention and limb health. Additionally, vacuum systems for prosthetic feet may be provided to further enhance the feel, fit, and function of the foot to the user for all types of lower limb amputation (e.g. above knee, below knee, etc.). Problems exist with vacuum systems including the noise of the electric motor and vacuum pump being disturbing to the user and those nearby and high maintenance requirements due to the complexity of the vacuum system.

SUMMARY

An exemplary vacuum system for a prosthetic foot may comprise a compressible member, a chamber located within the compressible member, and a valve system that connects to the prosthetic socket of the user. The valve system may comprise a valve housing, a pair of valves, an exhaust port, a fitting, an air passageway, and an air return.

Furthermore, the prosthetic foot may comprise a resilient bottom member having a first bottom end and a second bottom end, a resilient top member having a first top end and a second top end, wherein the first top end is connected to the first bottom end of the resilient bottom member, and wherein the resilient top member is connected to a mounting bracket and positioned over the resilient bottom member and directed towards the back of the prosthetic foot.

BRIEF DESCRIPTION OF THE DRAWINGS

A more complete understanding of the present invention may be derived by referring to the detailed description and claims when considered in connection with the following illustrative figures. In the following figures, like reference numbers refer to similar elements and steps throughout the figures.

Elements and steps in the figures are illustrated for simplicity and clarity and have not necessarily been rendered according to any particular sequence. For example, steps that may be performed concurrently or in a different order are illustrated in the figures to help to improve understanding of embodiments of the present technology.

Figure 1:
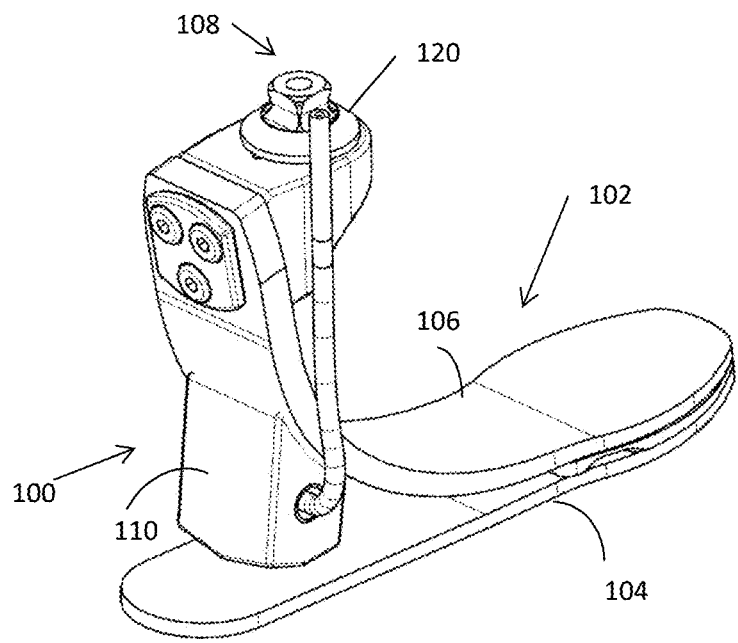
Figure 2:
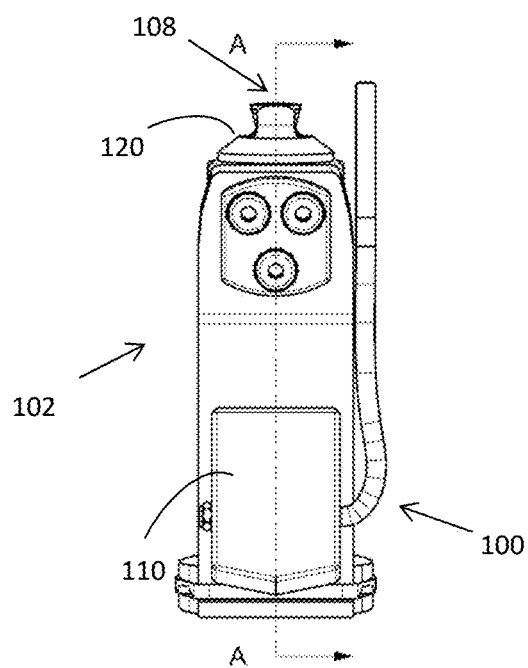
Figure 3:
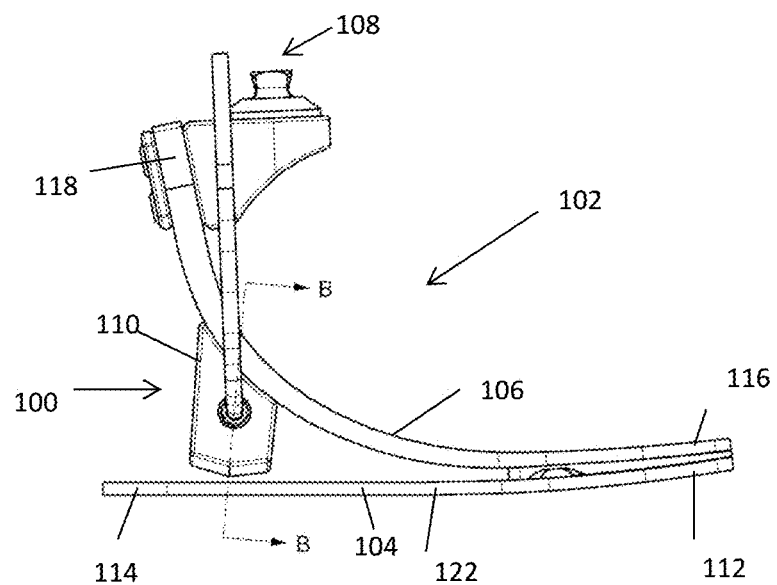
Figure 4:
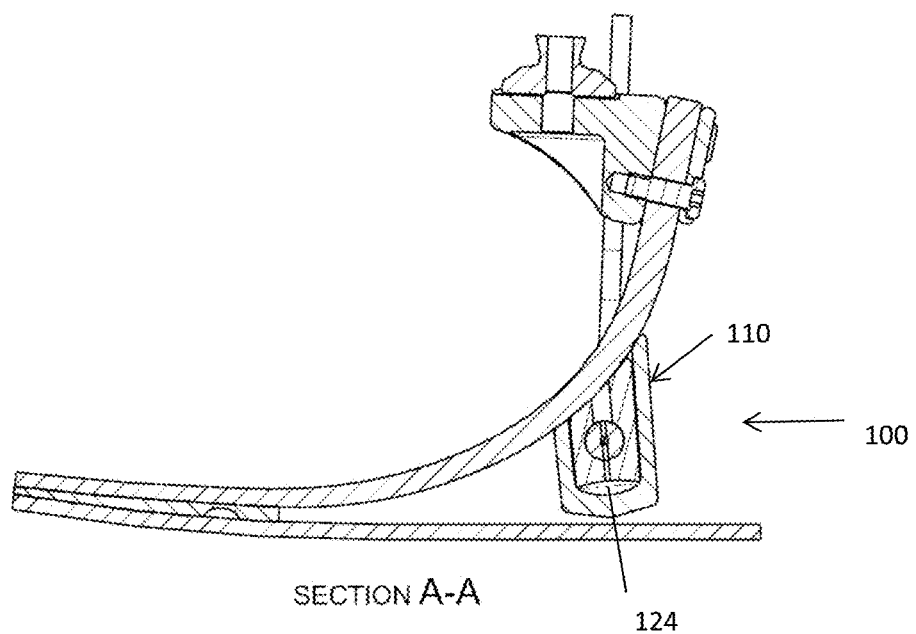
Figure 5:
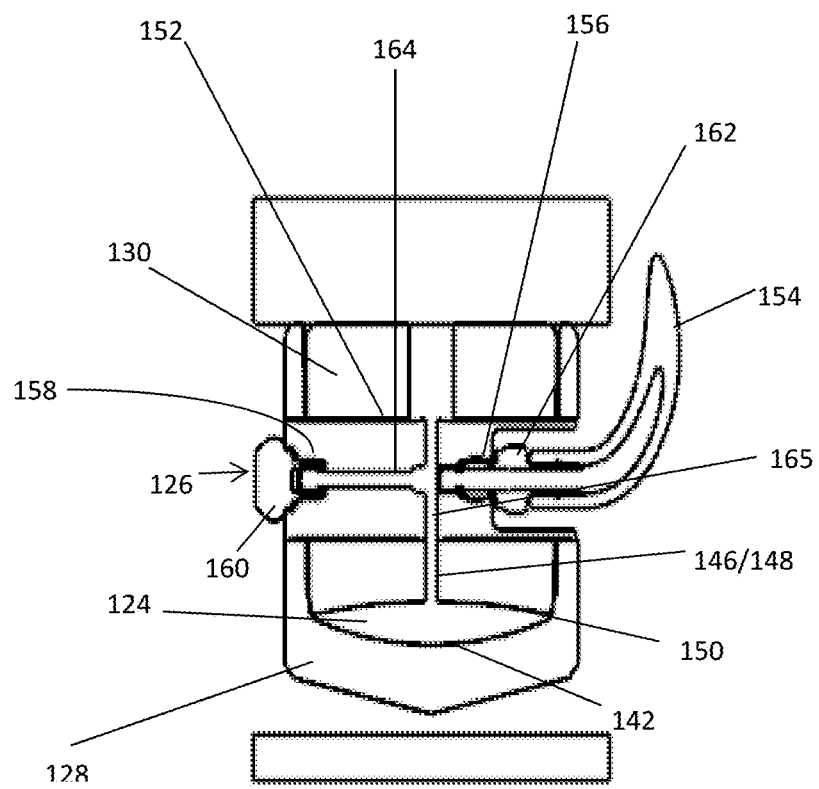
Figure 6:
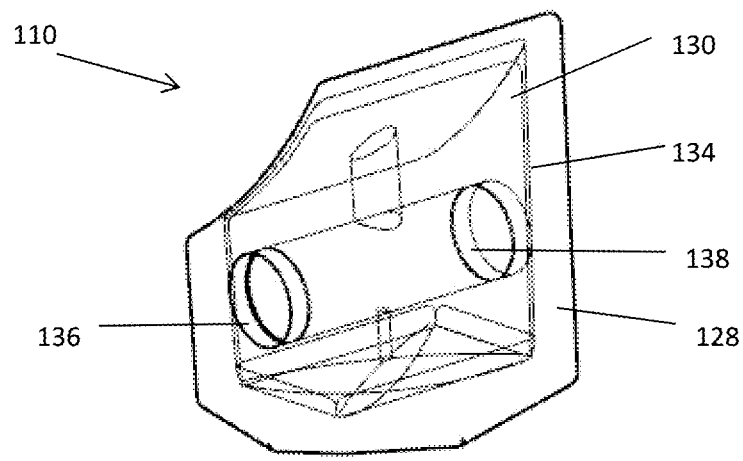
Figure 7:
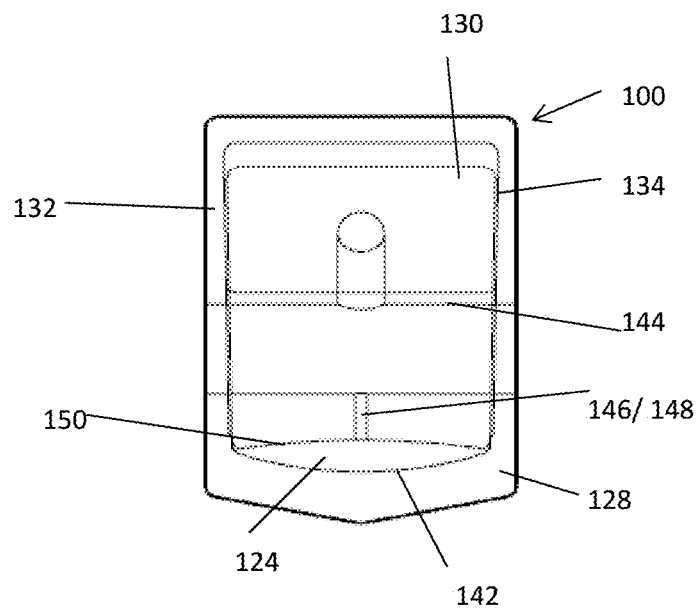
Figure 8:
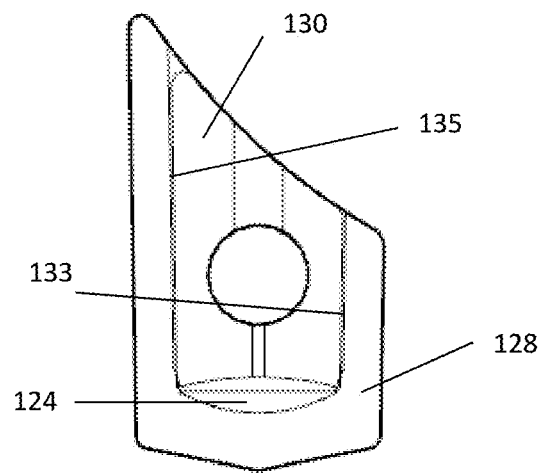
Figure 9:
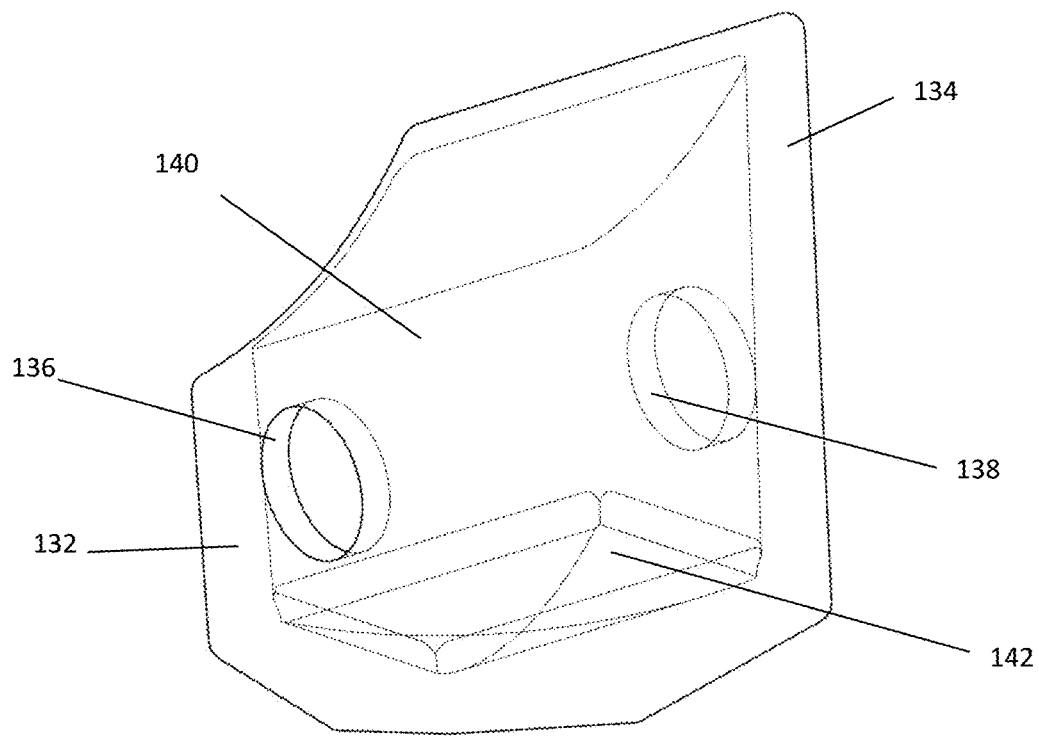
Figure 10:
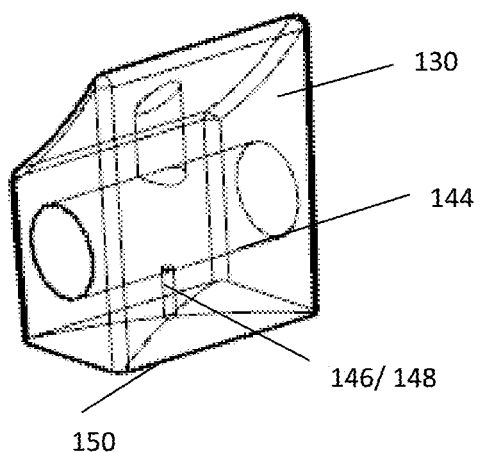
Figure 11:
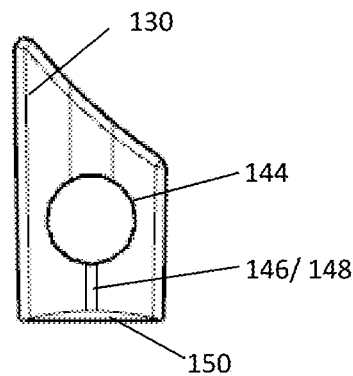
Figure 12:
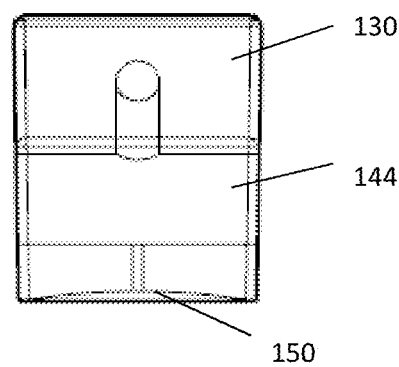
Figure 13:
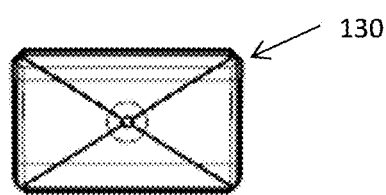
Figure 14A:
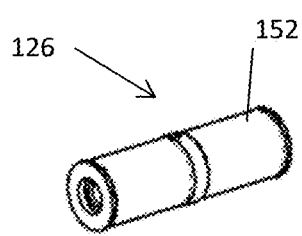
Figure 14B:
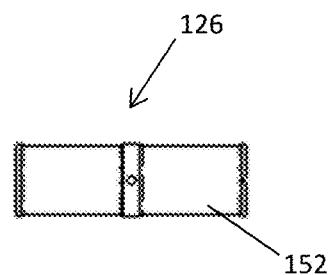
Figure 14C:
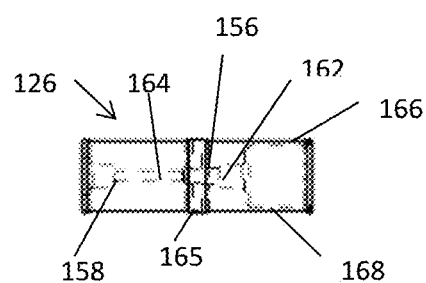
Figure 14D:
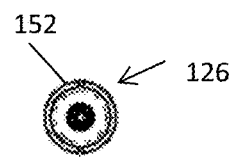
Figure 15:
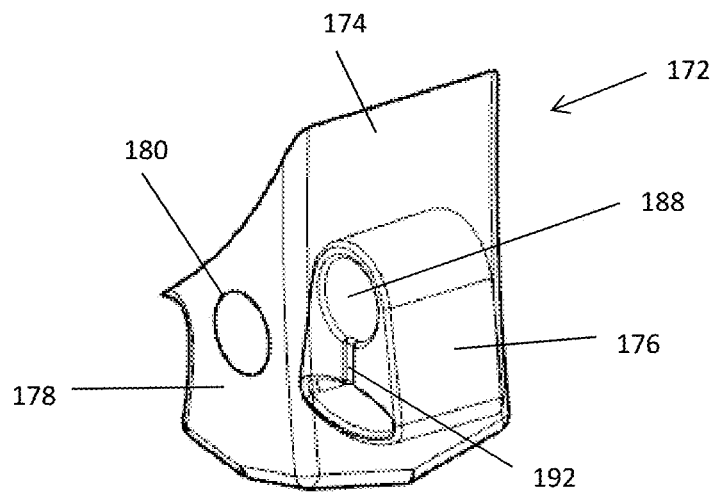
Figure 16:
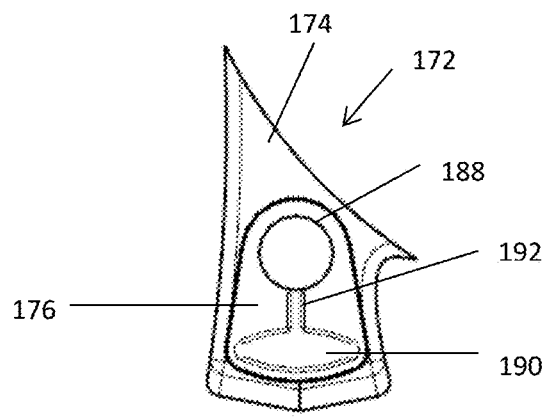
Figure 17:
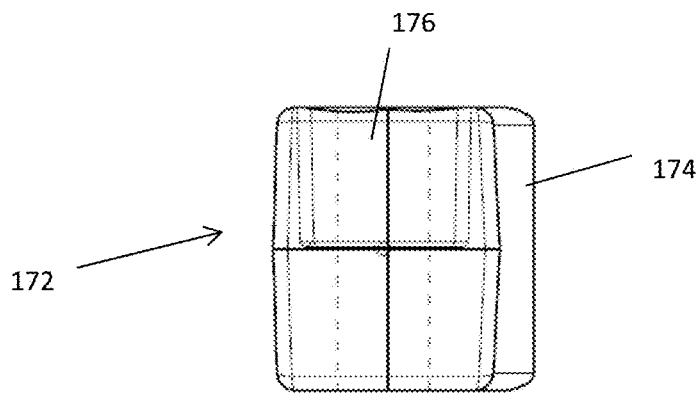
Figure 18:
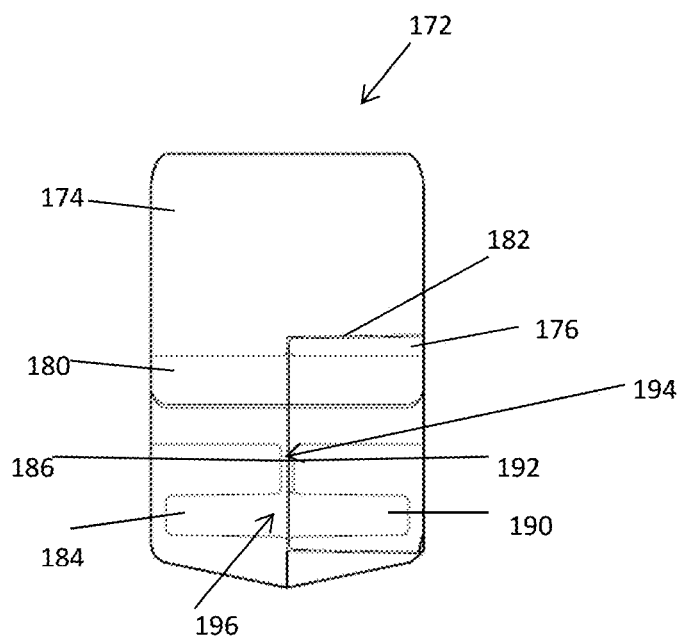
Figure 19:
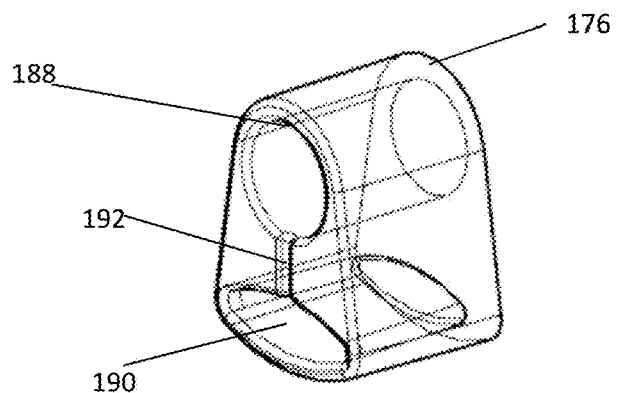
Figure 20:
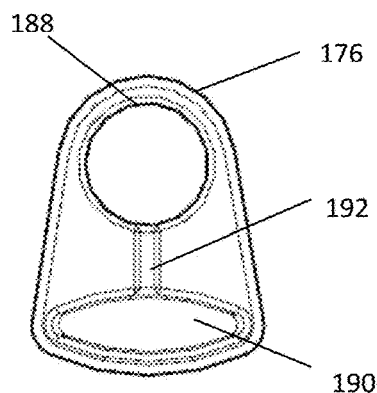
Figure 21:
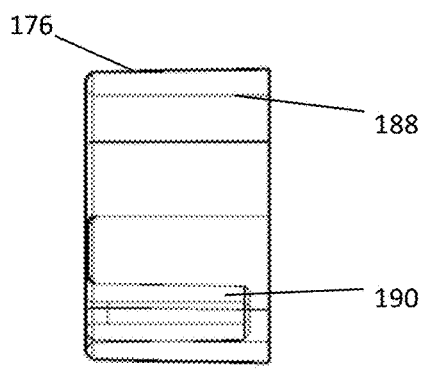
Figure 22:
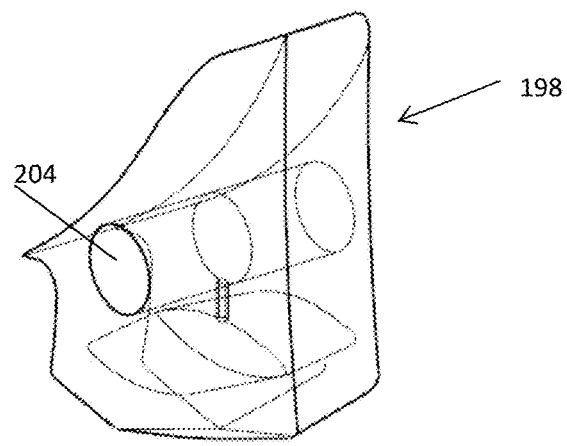
Figure 23:
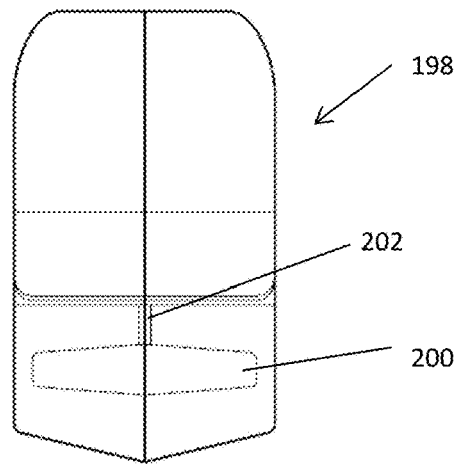
Figure 24:
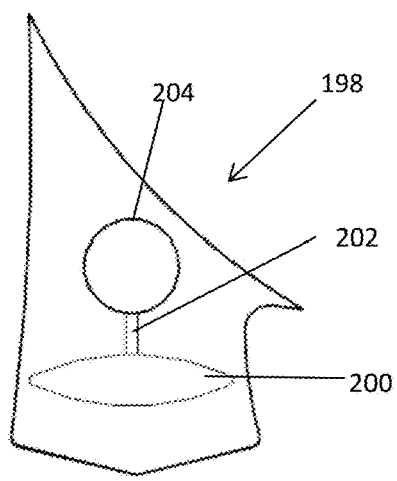

The figures described are for illustration purposes only and are not intended to limit the scope of the present disclosure in any way. Various aspects of the present invention may be more fully understood from the detailed description and the accompanying drawing figures, wherein:

FIG. 1 is a perspective view representatively illustrating a vacuum system on a prosthetic foot in accordance with exemplary embodiments of the present technology;

FIG. 2 is a rear view representatively illustrating the vacuum system on a prosthetic foot in accordance with exemplary embodiments of the present technology;

FIG. 3 is a side view representatively illustrating the vacuum system on a prosthetic foot in accordance with exemplary embodiments of the present technology;

FIG. 4 is a side, cross section view along the line A-A representatively illustrating the vacuum system on a prosthetic foot in accordance with exemplary embodiments of the present technology;

FIG. 5 is a partial rear, cross section view along the line B-B representatively illustrating the vacuum system on a prosthetic foot in accordance with exemplary embodiments of the present technology FIG. 6 is a perspective view of a compressible member with a heel member and a top insert in accordance with exemplary embodiments of the present technology;

FIG. 7 is a rear view of the compressible member with the heel member and the top insert in accordance with exemplary embodiments of the present technology;

FIG. 8 is a side view of the compressible member with the heel member and the top insert in accordance with exemplary embodiments of the present technology;

FIG. 9 is a perspective view of the heel member of the compressible member in accordance with exemplary embodiments of the present technology;

FIG. 10 is a perspective view of the top insert of the compressible member in accordance with exemplary embodiments of the present technology;

FIG. 11 is a side view of the top insert of the compressible member in accordance with exemplary embodiments of the present technology;

FIG. 12 is a rear view of the top insert of the compressible member in accordance with exemplary embodiments of the present technology;

FIG. 13 is a bottom view of the top insert of the compressible member in accordance with exemplary embodiments of the present technology;

FIGS. 14A-D show various view of a valve housing in accordance with exemplary embodiments of the present technology;

FIG. 15 is a perspective view of an additional embodiment of a compressible member with a heel member and a side insert in accordance with exemplary embodiments of the present technology;

FIG. 16 is a side view of the additional embodiment of the compressible member with the heel member with the side insert removed in accordance with exemplary embodiments of the present technology;

FIG. 17 is a bottom view of the additional embodiment of the compressible member with the heel member and the side insert in accordance with exemplary embodiments of the present technology;

FIG. 18 is a rear view of the additional embodiment of the compressible member with the heel member and the side insert in accordance with exemplary embodiments of the present technology;

FIG. 19 is a perspective view of the side insert of the compressible member in accordance with exemplary embodiments of the present technology;

FIG. 20 is a side view of the side insert of the compressible member in accordance with exemplary embodiments of the present technology;

FIG. 21 is a rear view of the side insert of the compressible member in accordance with exemplary embodiments of the present technology;

FIG. 22 is a perspective view of an additional embodiment of a compressible member in accordance with exemplary embodiments of the present technology;

FIG. 23 is a rear view of the additional embodiment of the compressible member in accordance with exemplary embodiments of the present technology; and FIG. 24 is a side view of the additional embodiment of the compressible member in accordance with exemplary embodiments of the present technology.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may be used with a prosthetic foot for various amputation types (above knee, below knee, etc.) In addition, the present technology may be practiced in conjunction with any number of materials and methods of manufacture and the system described is merely one exemplary application for the technology.

While exemplary embodiments are described herein in sufficient detail to enable those skilled in the art to practice the invention, it should be understood that other embodiments may be realized and that logical structural, material, and mechanical changes may be made without departing from the spirit and scope of the invention. This disclosure, its aspects and implementations, are not limited to the specific components or assembly procedures disclosed herein. Many additional components and assembly procedures known in the art consistent with the intended apparatus will become apparent for use with implementations of vacuum systems for prosthetic feet. Thus, the following descriptions are not intended as a limitation on the use or applicability of the invention, but instead, are provided merely to enable a full and complete description of exemplary embodiments.

Briefly, in accordance with exemplary embodiments, a vacuum system for a prosthetic foot is illustrated, which allows for a more comfortable fit of the residual limb to the prosthetic socket of a user. Additionally, studies have shown that elevated vacuum above a certain level is beneficial for residual limb health and maintaining residual limb volume.

A typical prosthetic foot stores energy during the gait cycle and transfers the return potential energy in order to "put a spring in your step." The roll through of a prosthetic foot is defined in the gait cycle as the process from the heel-strike phase to the mid-stance phase to the toe-off phase. The heel-strike phase begins when the heel, or rear portion of the foot touches the ground, and includes the loading response on the foot. The mid-stance phase is when the foot is flat on the ground and the body's center of gravity is over the foot. The toe-off phase is the finish of the stance phase and ends when the tip of the foot is the only portion in contact with the ground, and the load is entirely on the toe/tip of the foot. This is just prior to the swing phase, which constitutes the other half of the gait cycle.

As the user moves through the stance phase portion of the gait cycle the tibia portion of the leg, or that section of the leg defined below the knee, rotates through in relation to the ground. If the mid-stance phase is defined as the lower leg at 90 degrees to the ground, then looking at the side view of an individual, the angle of the lower leg at the heel-strike phase may occur at approximately 65 degrees and the angle of the lower leg at the toe-off phase may occur at approximately 110 degrees. The rotation of the lower leg on the theoretical ankle is notated as tibial progression or lower leg progression during the stance phase. It is through the loads imparted by a user to a prosthetic foot through the stance phase of the gait cycle that a vacuum system may be powered to provide a better fit and feel for the connection of the residual limb of the user and the prosthetic socket throughout the gait cycle.

In accordance with various embodiments and with reference to FIGS. 1-7, a vacuum system 100 for a prosthetic foot 102 is shown. The prosthetic foot 102 may comprise a resilient bottom member 104, a resilient top member 106, a connection point 108 attached to the top member 106 and configured for attachment to a user, and a compressible member 110. The resilient bottom member 104 may have a front end 112 and a rear end 114. The resilient top member 106 may have a front end 116 and a rear top end 118. Further, the front end 112 of the resilient top member 106 can be connected to the front end 116 of the resilient bottom member 104, while the resilient top member 106 can be positioned over the resilient bottom member 104 and directed towards the rear of the prosthetic foot 102.

The connection point 108 may be coupled to the rear top end 118 of the resilient top member and comprise a mounting portion 120. The mounting portion 120 may comprise a spherical dome and an attachment portion, which is a standard male pyramid adapter used in the prosthetic industry. The pyramid adapter may be coupled with a standard receiver used in the practice of prosthetics, for example, a Staats style attachment, which is commonly known in the prosthetic industry. The mounting portion 120 may use a standard receiver adapter, as understood by one of ordinary skill in the art. According to various embodiments the mounting portion 120 may facilitate attachment to the residual limb of the user. The mounting portion 120 may comprise a centerline that is aligned with the weight line of the user.

Moreover and with renewed reference to FIG. 1, the top member 106, bottom member 104, and compressible member 110 transfer energy between themselves in a natural, true foot manner. The loading response during the heel strike phase compresses compressible member 110 and top member 106, which in turn passes energy into, and causes a deflection of, a rear portion of bottom member 104. Energy is transferred towards the front of prosthetic foot 100 during the mid-stance phase. Furthermore, an upward deflection of at least one of bottom member 104 and top member 106 stores energy during the transition from the mid-stance phase to the toe-off phase of the gait cycle.

With respect to the walking motion, the prosthetic foot 102 is configured to increase the surface-to-foot contact through the gait cycle. The increased surface contact allows for a smoother gait cycle, and increases stability in comparison to the typical prior art prosthetics. In exemplary embodiments, the underside of bottom member 104 has different contours that provide increased surface contact for different types of uses.

The resilient bottom member 104 of the prosthetic foot 102 can have various shapes depending on desired use. The desired use may include prosthetic feet for above-knee amputees or prosthetic feet for below-knee amputees. In various embodiments, the prosthetic foot 102 for above-knee amputees may comprise a bottom member 104 having a curved bottom with no inflection point. In one embodiment, the prosthetic foot 102 comprises a resilient bottom member 104 having a partially curved portion from the front end 112 to the rear end 114 of the resilient bottom member 104. In various embodiments, the bottom member 104 may comprise a constant arc due to single radius forming the partial curve of the bottom member 104. In other various embodiments, the curve of the bottom member 104 can be designed as a spline of variable radii. The curve of bottom member 104 in above-knee prosthetic foot facilitates keeping an artificial knee stable because the forces substantially restrict the knee from bending. The curved bottom member 104 enables a rocking motion even if the artificial knee is hyper-extended.

Similarly, the prosthetic foot 102 for below-knee amputees may comprises a bottom member 104 having a partially curved front portion and a substantially linear rear portion. In one embodiment, the prosthetic foot 102 comprises a resilient bottom member 104 having a partially curved portion from the front end 112 to a middle portion 122 and a substantially linear rear portion from the middle portion 122 to the rear end 114 of the resilient bottom member 104. The front portion from the front end 112 to the middle portion 122 of resilient bottom member 104 may have a constant arc due to single radius forming the partial curve. In various embodiments, the front portion from the front end 112 to the middle portion 122 of resilient bottom member 104 can have a curve designed as a spline of variable radii. In accordance with various embodiments, the rear portion from the middle portion 122 to the rear end 114 of the resilient bottom member 104 can be substantially straight and tangent to the front portion such that bottom member 104 does not have an inflection point. A straight rear portion and a curved front portion of bottom member 104 facilitates rotation of the tibia progressing the natural rotation of the knee forward and preventing hyper-extension of the knee.

In accordance with an exemplary embodiment, resilient bottom and top members 104, 106 may be made of glass fiber composite. The glass fiber composite may be a glass reinforced unidirectional fiber composite. In one embodiment, the fiber composite material is made of multiple layers of unidirectional fibers and resin to produce a strong and flexible material. The fibers may be glass fibers or carbon fibers. Specifically, layers of fiber are impregnated with the resin, and a glass reinforcement layer can be positioned between at least two fiber weave layers. Typically, several layers of the unidirectional fibers or tape are layered together to achieve the desired strength and flexibility. Further, in various embodiments the layers of unidirectional fibers or tape can be oriented at various angles.

The vacuum system 100 may be used with any conventional prosthetic leg (consisting of socket, pylon, etc.). The vacuum system 100 may be configured to connect to any commercially available prosthetic socket designed to work with a vacuum attachment apparatus. Specifically, the vacuum system 100 will connect to an elevated vacuum suspension setup and also should also work with any commercially available prosthetic socket designed for passive suction suspension.

In one embodiment, the vacuum system 100 may be utilized with the existing compressible member 110. In another embodiment, the vacuum system may be added to a foot without a compressible member or used in conjunction with an existing compressible member in a prosthetic foot.

Referring to FIGS. 5-8, the vacuum system 100 for a prosthetic foot may comprise a compressible member 110, a chamber 124 located within the compressible member 110, and a valve system 126 that connects to the prosthetic socket of the user (not shown).

The compressible member 110 may comprise a heel member 128 and a top plug insert 130. In various embodiments, the top plug insert 130 and the heel member 128 can be any suitable shape as contemplated by one of ordinary skill in the art. In various embodiments, the top plug insert 130 may be inserted within the heel member 128 to form the chamber. As shown in FIG. 9, the heel member 128 may comprise a pair of sidewalls 132, 134 with internal bores 136, 138, a front wall 133, a rear wall 135, and a cavity 140 that receives the top plug insert 130. The cavity 140 may comprise an internal surface 142 or any other suitable shape.

Referring now to FIGS. 6, 7, and 10, the top plug insert 130 may comprise an internal bore 144 and a void 146 that function as an air passageway 148. The top plug insert 130 may comprise a concave lower surface 150. When the top plug insert 130 is placed within the cavity 140 the internal bores 136, 138 of heel member 128 align with the internal bore 144 of the top plug insert 130 to receive the valve system 126, shown in FIG. 5. Additionally, the concave internal surface 142 of the cavity 140 and the concave lower surface 150 of the top plug insert 130 form the chamber 124. In various embodiments, the chamber 124 may be generally in the shape of an oblate spheroid, a short or flattened octahedron, a rectangular pillow shape, or any other shape that can be collapsed on itself when a vertical force is applied.

The top plug insert 130 is both bonded in place and mechanically locked by the valve system 126 which protrudes through the internal bores 136, 138 of heel member 128 and the internal bore 144 of the top plug insert 130. The top plug insert 130 may be bonded to the heel member 128 using an adhesive appropriate for bonding two elastomeric deformable materials, such as rubber, together. In various embodiments, the top plug insert 130 and the cavity 140 within the heel member 128 can be any suitable shape as contemplated by one of ordinary skill in the art as long as the top plug insert 130 is capable of being inserted within the cavity 140 within the heel member 128 to create the chamber 124.

In various embodiments, the chamber 124 may be located within the compressible member 110 and is connected to the valve system 126 by the air passageway 148. In one embodiment, the chamber 124 may be formed between the internal surface 142 of the heel member 128 and the lower surface 150 of the top plug insert 130. In one embodiment, chamber 124 may comprise a generally rectangular in shape as shown in FIG. 6. When viewed from the rear, as shown in FIGS. 5 and 7, the chamber 124 is roughly elliptical in shape, which allows the chamber to fully collapse when loaded. In another embodiment, the chamber 124 is generally rectangular when viewed from the side and from the back. In another embodiment chamber 124 may comprise an upside-down T shape when viewed from the side. In one embodiment the volume of chamber 124 is approximately 0.1 to 0.25 cubic inches. It should be understood that any volume contemplated may be used as long as the volume is configured to provide enough back pressure to seal the socket to the residual limb.

The chamber 124 may be connected to the valve system 126 by way of air passageway 148. In various embodiments, the air passageway 148 can be a void in the top plug insert 130 or a separate tube located inside the top plug insert 130. The separate tube comprising air passageway 148 may be a small diameter stainless steel tubing, or small diameter carbon fiber tubing, small diameter flexible plastic tubing, and the like. Alternatively, air passageway 148 may connect chamber 124 to the valve system 126 in a way external to compressible member 110.

It should be noted that in an exemplary embodiment, that there is a single air passageway 148 connecting the chamber 124 to the valve system 126. In various embodiments the air passageway 148 may be bi-directional. Furthermore, the chamber 124 contemplated above may exist solely between the internal surface 142 of the heel member 128 and the lower surface 150 of the top plug insert 130 and may be any suitable shape that can compress and/or collapse on itself. Specifically, in one embodiment, there is not any contemplated internal membrane located within the chamber 124 between the internal surface 142 of the heel member 128 and the lower surface 150 of the top plug insert 130.

In various embodiments and referring now to FIGS. 5-7, the valve system 126 may comprise a valve housing 152 and an air return 154. The valve housing 152 may comprise a pair of valves 156, 158, an exhaust port 160, and a fitting 162. An air chamber 164 connects the pair of valves 156, 158 and allows for air to travel therebetween. A valve housing passageway 165 connects the passageway 148 to the air chamber 164. Air may travel into the housing through valve 156 and out through valve 158. The air return 154 connects to the prosthetic socket of the user, which contains the vacuum attachment apparatus. The air return 154 may comprise standard ⅛ inch diameter tubing used to connect vacuum systems to prosthetic sockets.

In various embodiments, the valve housing 152 may be located within the internal bores 136, 138 of the heel member 128 and the internal bore 144 of the top plug insert 130 of the compressible member 110. In one embodiment, the internal bore 144 of the top plug insert 130 is located within the compressible member 110 and between the sidewalls 132, 134, the front wall 133, and the rear wall 135 of the heel member 128 of the compressible member 110. In one embodiment, the internal bore 144 of the top plug insert 130 is located within the compressible member 110 and between the sidewalls 132, 134, the front wall 133, and the rear wall 135 of the heel member 128 of the compressible member 110 and oriented substantially horizontally therewithin. While the shape of the valve housing 152 of the valve system 126 is shown as generally cylindrical, any configuration and shape may be contemplated. The valve housing 152 may comprise the fitting 162 located at a first end and the exhaust port 160 located at a second end opposite the first end. The internal bores 136, 138 of the heel member 128 and the internal bore 144 of the top plug insert 130 and the valve housing 152 are typically designed with generally the same shape and dimensions such that a tight fit of the valve housing 152 within the internal bore(s) exists.

The fitting 162 may be coupled to the air return 154 at the first end, which in turn may be connected to the user's prosthetic socket that contains the vacuum attachment apparatus (not shown). The first valve 156 may be coupled to the second end of the fitting 162 by any suitable manner. In one embodiment, the fitting 162 has a ⅛ inch internal diameter tube fitting at the first end, and 10-32 UNF threaded connection with an O-ring gasket that seals a mating face 166 of the fitting 162 to an internal wall 168 of the valve housing 152 when fully tightened down and installed within the inner bore 130. An example of the fitting 162 is produced by Pneumadyne® and is part number EB-30-250.

The exhaust port 160 may be coupled to the second end of the valve housing 152. The exhaust port 160 may be coupled to the valve housing 152 in any suitable manner. In one embodiment, the exhaust port 160 may comprise a filtered exhaust port through which the air exiting travels to the atmosphere at a first end of the exhaust port. Some examples of the exhaust port are McMaster-Carr® part number 9833K18 or alternatively Industrial Specialties Mfg. part number BV-1032M-40-B. In one embodiment, the McMaster-Carr® part is sealed using Teflon® tape on the threads of the fitting. In one embodiment, the Industrial Specialties Mfg. part has an O-ring gasket that seals the mating face to the housing when fully tightened within the valve housing 152.

In various embodiments, the second valve 158 may be located adjacent an internal end of the exhaust port 160. The first and second valves 156, 158 may comprise one-way duckbill valves. The one-way duckbill valve design has a very low cracking pressure (to allow air in the designed direction of travel) and does not allow air to travel in the reverse direction. In one embodiment, the one-way duckbill valve is produced by Minivalve International, part number DU027.002-154. The second valve 158 allows air to exit the valve housing 152 into the atmosphere, while the first valve 156 permits air to enter valve housing 152, as will be discussed in detail below. The area between the first valve 156 and second valve 158 may comprise an open-air chamber 164 that allows air to flow between the two valves. This open air chamber 164 is connected to air passageway 148 by the valve housing passageway 165 and provides free air flow to the chamber 124 within the compressible member 110.

In operation, when a downward force is applied to the prosthetic foot 102, the compressible member 110 and the chamber 124 located therein are compressed when they come into contact with the resilient bottom member 104. The compression of the chamber 124 within the compressible member 110 forces air out of the chamber 124 up through air passageway 148 and into valve housing 152. The pressurized air exits the valve housing 152 through the second valve 158 and the exhaust port 160. When the downward force on the prosthetic foot 102 is reduced or eliminated, the compressible member 110 returns the chamber 124 back to a maximum volume state due to the elastic properties of compressible member 110. The elastic properties and geometry of compressible member 110 allow chamber 124 to expand back to the initial volume when the downward force is eliminated or reduced to the point that the compressible member 110 is no long in contact with the resilient bottom member 104. The second valve 158 then closes and prevents a backflow of air into the valve housing 152 through the exhaust port 160. This causes a negative pressure in valve housing 152. The negative pressure draws air into the valve housing 152 through first valve 156 by way of the fitting 162 and the air return 154. The air return 154 is connected to a prosthetic socket that is designed for an elevated vacuum suspension and the like. The elevated vacuum suspension socket is a commercially available prosthetic socket that uses an elevated vacuum level inside the socket to secure the socket to the amputee's residual limb.

In various embodiments, the compressible member 110 comprises an elastomeric bumper member having a tapered surface configured to contact the resilient bottom member 104 and attached to an underside of a rear top end of the upper member 106. The compressible member 110 can be vertically oriented with respect to the prosthetic foot 102. The compressible member 110 can act as a heel shock for absorbing force on the downward strike during the user's stride and returns energy during the rest of the gait cycle.

In various embodiments, the compressible member 110 can be made from an elastomeric material. In one embodiment, the elastomeric material may be constructed of natural, synthetic or a hybrid mixture of both natural and synthetic rubber. The elastomeric material has about 80% or greater energy return. In another embodiment, the elastomeric material has about 90% or greater energy return. The compressible member 110 can be designed to behave similar to a non-linear spring, thereby allowing larger deflection of the posterior toe during the heel strike. The progressive "spring rate" may lead to a soft initial heel strike but quickly and gently arrests deflection as the compressible member 110 compresses. One benefit of the compressible member 110 is being relatively lightweight in comparison to a prosthetic foot with coiled springs.

As seen in FIG. 4, the compressible member 110 can be located posterior to a vertical axis of the connection point of the mounting portion 120. This enhances the aforementioned and desirable trait of tibial progression. The compressible member 110 can be attached to the underside of the resilient top member 106 in various manners. For example, the compressible member 110 can be fixedly attached using adhesive or fasteners, such as screws. In another example, the compressible member 110 may be detachable using fasteners for replacement purposes. Moreover, in other embodiments, the compressible member 110 can be attached to various locations on the underside of the resilient top member 106 or topside of the resilient bottom member 104.

In various embodiments, the prosthetic foot 100 in a static mode has a gap between the compressible member 110 and the resilient bottom member 104. For example, a gap of about 1/10 inch may be present between the compressible member 110 and the resilient bottom member 104. In other various methods, the compressible member 110 can be in contact with both the resilient top member 106 and the resilient bottom member 104 when the prosthetic foot 100 is in a static position. The lack of a gap results in the compressible member 110 being continuously compressed during the gait cycle, though the compressible member 110 is a compression member and not a tension member since the compressible member 110 is only attached to either the top member 106 or the resilient bottom member 104. It is important to the design of the compressible member such that it is only attached to one or the other of the resilient top member 106 and the resilient bottom member 104 and not to both. Connecting the compressible member 110 to both the resilient top and bottom members 106, 104 creates almost a triangle structure, which is very stiff.

The compressible member 110 can be in many shapes. In various embodiments, the detached portion of the compressible member 110 may have a conical, rectangular, or pyramid shape. The tapered surface of the compressible member 110 can terminate in an apex or hemispherical shape, and the apex can be configured to contact the resilient bottom member 104 in response to deflection of the prosthetic foot 100. Moreover, in various embodiments, the compressible member 110 can terminate in multiple points. The tapered compressible member 110 facilitates a damping of vibration and sound generated during heel strike or release. Furthermore, in various embodiments the extruding portion of the compressible member 110 may be any shape that is non-flat surface. Further, a non-flat surface enhances lateral flexibility if the heel strike is not vertical.

The prosthetic foot 100 can be adjusted to accommodate a user in part by adjusting characteristics of the compressible member 110. For example, in various embodiments, the durometer of the compressible member 110 can be increased for users with more heel strike force, which may be caused by additional weight or dynamic activity. A heavier user may be better-suited using a compressible member 110 with a large cross-sectional area compared to a lighter user using a compressible member 110 with a small cross-sectional area. The adjustable durometer of the elastomeric material used for the compressible member 110 allows the adjustment of spring rate of the elastomeric heel based on user needs such as activity level, compliance level, weight changes, and the like. Increased durometer can also adjust the ability of chamber 124 to return to the initial volume after being compressed.

In various embodiments, and referring now to FIGS. 15-21, an additional embodiment of a compressible member 172 may comprise a heel member 174 and a side plug insert 176. The valve system 126 described above may be implemented with the compressible member 172. The heel member 174 comprises a sidewall 178 with internal bore 180, a cavity 182 that receives the side plug insert 176 and a pair of internal voids 184, 186.

The side plug insert 176 may comprise an internal bore 188 and a pair of voids 190, 192. When the side plug insert 176 is placed within the cavity 182 the internal bore 180 of heel member 174 aligns with the internal bore 188 of the side plug insert 176 to receive the valve system 126 (not shown). Additionally, the pair of internal voids 190, 192 of the side plug insert and the pair of internal voids 184, 186 of the heel member 174 combine to form an air passageway 194 and a chamber 196.

The side plug insert 176 is both bonded in place as discussed above, and mechanically locked by the valve system 126 which protrudes through the internal bore 180 of heel member 174 and the internal bore 188 of the side plug insert 176. It should be understood that orientation of the side plug insert and heel member may be reversed, for example, the side plug insert can be placed in a cavity on either side of the heel member.

Referring now to FIGS. 22-24, the vacuum system 100 for a prosthetic foot may comprise a compressible member 198, a chamber 200 located within the compressible member 198, and the valve system 126 that connects to the prosthetic socket of the user (not shown).

In various embodiments the chamber 200 may be located within the compressible member 198 and is connected to the valve system 126 by an air passageway 202. The valve system 126 described above may be implemented with a bore 204 located within the compressible member 198. In one embodiment, the chamber 200 may be formed by molding in a void in each left and right halves of compressible member 198 and consequently bonding the left and right halves of compressible member 198 into a single piece. In one embodiment, the chamber 200 may be formed by molding in a void and sealing the void at one end with a separate piece made of the same material as the compressible member 198 and bonding it into place. In various embodiments, chamber 200 may be formed by 3D printing the material or by a material removal process, such as, cutting or machining and drilling the material. In one embodiment, chamber 200 may comprise a generally rectangular in shape when viewed from the top. When viewed from the rear and side, as shown in FIGS. 23 and 24, the chamber 200 is roughly elliptical in shape, which allows the chamber 200 to fully collapse when loaded. In another embodiment, chamber 200 is generally rectangular when viewed from the side and from the back. In another embodiment, the chamber 200 may comprise an upside-down T shape when viewed from the side or rear. In one embodiment the volume of chamber 200 is approximately 0.1 to 0.25 cubic inches. It should be understood that any volume contemplated may be used as long as the volume is configured to provide enough back pressure to seal the socket to the residual limb.

The chamber 200 may be connected to valve housing 152 by way of the air passageway 202. In various embodiments, the air passageway 202 can be a void in the heel mold or a separate tube located inside compressible member 198 or located between the left and right halves of the compressible member 198. The separate tube comprising air passageway 202 may be small diameter stainless steel tubing, or small diameter carbon fiber tubing, small diameter flexible plastic tubing, and the like. Alternatively, air passageway 202 may connect chamber 200 to valve housing 152 in a way external to compressible member 198.

It should be understood that the compressible members 172, 198 are shaped, located, oriented, constructed, and attached to the prosthetic foot similarly to the compressible member 110 discussed above. It should be understood that the compressible members 172, 198 also function similarly to the compressible member 110 discussed above.

The technology has been described with reference to specific exemplary embodiments. Various modifications and changes, however, may be made without departing from the scope of the present technology. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any order, unless otherwise expressly specified, and are not limited to the explicit order presented in the specific examples. Additionally, the components and/or elements recited in any apparatus embodiment may be assembled or otherwise operationally configured in a variety of permutations to produce substantially the same result as the present technology and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to a preferred embodiment. However, changes and modifications may be made to the preferred embodiment without departing from the scope of the present technology. These and other changes or modifications are intended to be included within the scope of the present technology, as expressed in the following claims.

The invention claimed is:

1. A prosthetic foot for use with a prosthetic socket containing a vacuum attachment apparatus and configured to attach to a residual limb, the prosthetic foot comprising:
    a resilient bottom member comprising a front end and a rear end;
    a resilient top member comprising a front end and a rear end, wherein the front end of the resilient top member is connected to the front end of the resilient bottom member, and wherein the resilient top member is positioned over the resilient bottom member;
    a vacuum system coupled to an underside of the top member, the vacuum system comprising:
        a compressible member comprising:
            a heel member comprising a pair of sidewalls, a front wall, a rear wall, and a cavity; and
            a top plug insert that is received between the sidewalls and within the cavity to form a chamber;
        a valve system received within the compressible member;
        a passageway connecting the valve system and the chamber; and an air return coupled to the valve system and the vacuum attachment apparatus.

2. The prosthetic foot of claim 1, wherein an upper internal surface of the cavity and a lower surface of the top plug insert form the chamber.

3. The prosthetic foot of claim 1, wherein each of the pair of sidewalls of the heel member comprises an internal bore.

4. The prosthetic foot of claim 3, wherein the top plug insert comprises an internal bore.

5. The prosthetic foot of claim 4, wherein when the top plug insert is received within the heel member, the internal bores of the heel member align with the internal bore of the top plug insert to receive the valve system and lock the top plug insert within the heel member.

6. The prosthetic foot of claim 1, wherein the valve system comprised:
   a housing comprising a first end and a second end;
   a first valve located within the housing at the first end;
   a second valve located within the housing at the second end;
   an air chamber located within the housing between the first valve and the second valve;
   an exhaust port coupled to the second valve; and
   the air return coupled to the first valve.

7. The prosthetic foot of claim 6, wherein the passageway is in air communication with the cavity in the compressible member and the air chamber in the valve system housing.

8. The prosthetic foot of claim 1, wherein the top plug insert is coupled within the heel member.

9. The prosthetic foot of claim 8, wherein the top plug insert is bonded within the heel member.

10. The prosthetic foot of claim 9, wherein the top plug insert is bonded within the heel member using an adhesive.

11. The prosthetic foot of claim 1, wherein the chamber is compressed when the compressible member contacts the resilient bottom member in response to an applied downward force on the resilient top member.

12. The prosthetic foot of claim 11, wherein the compression of the chamber within the compressible member forces air out of the chamber through the passageway and out of the valve system.

13. The prosthetic foot of claim 11, wherein upon removal of the downward force, the chamber expands causing a negative pressure within the valve assembly and activates the vacuum attachment apparatus through the air return.

14. The prosthetic foot of claim 13, wherein the chamber is configured to expand due to elastomeric properties of the compressible member.

15. A prosthetic foot for use with a prosthetic socket containing a vacuum attachment apparatus and configured to attach to a residual limb, the prosthetic foot comprising:
   a resilient bottom member comprising a front end and a rear end;
   a resilient top member comprising a front end and a rear end, wherein the front end of the resilient top member is connected to the front end of the resilient bottom member; and
   a vacuum system coupled to an underside of the rear end of the top member the vacuum system comprising:
      a compressible member, comprising:
         a heel member comprising a pair of sidewalls, a front wall, a rear wall, and a cavity; and
         a top plug insert that is received between the sidewalls and within the cavity to form a chamber;
      a valve system received within the compressible member;
      a single passageway connecting the valve system and the chamber; and
      an air return coupled to the valve system and the vacuum attachment apparatus.

16. The prosthetic foot of claim 15, wherein an upper internal surface of the cavity and a lower surface of the top plug insert form the chamber.

17. The prosthetic foot of claim 16, wherein the chamber is compressed when the compressible member contacts the resilient bottom member in response to an applied downward force on the resilient top member.

18. The prosthetic foot of claim 16, wherein upon removal of the downward force, the chamber expands causing a negative pressure within the valve assembly and activates the vacuum attachment apparatus through the air return.

19. A vacuum system for use with a prosthetic socket containing a vacuum attachment apparatus and a prosthetic foot comprising a resilient bottom member and a resilient top member, wherein an underside of a front end of the resilient top member is coupled to a front end of the resilient bottom member, the vacuum system comprising:
   a compressible member configured to be coupled to the underside of the rear end of the resilient top member, the compressible member comprising:
      a heel member comprising a pair of sidewalls, a front wall, a rear wall, and a cavity; and
      a top plug insert that is received between the sidewalls, the front wall, the rear wall and within the cavity to form a chamber;
   a valve system received within the compressible member;
   a single passageway connecting the valve system and the chamber; and
   an air return configured to couple to the valve system and the vacuum attachment apparatus,
   wherein the chamber is configured to be compressed when the compressible member contacts the resilient bottom member in response to an applied downward force on the resilient top member, and wherein the chamber is configured so as to expand upon removal of the downward force which in turn would cause a negative pressure within the valve assembly and activation of the vacuum attachment apparatus through the air return.

* * * * *